United States Patent
Chauhan et al.

(10) Patent No.: US 6,870,038 B2
(45) Date of Patent: Mar. 22, 2005

(54) **ISOLATION AND EXPRESSION OF A GENE FOR A NITRILASE FROM *ACIDOVORAX FACILIS* 72W**

(75) Inventors: Sarita Chauhan, Landenberg, PA (US); Robert Dicosimo, Rockland, DE (US); Robert D. Fallon, Elkton, MD (US); John E. Gavagan, Wilmington, DE (US); Mark S. Payne, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/823,373

(22) Filed: Mar. 30, 2001

(65) Prior Publication Data

US 2004/0197772 A1 Oct. 7, 2004

Related U.S. Application Data

(60) Provisional application No. 60/193,707, filed on Mar. 31, 2000.

(51) Int. Cl.[7] .................. C07H 21/02; C07H 21/04; C12Q 1/68
(52) U.S. Cl. .................. 536/23.1; 536/24.3; 435/6; 435/240.2; 435/320.1
(58) Field of Search .................. 435/6, 240.2, 320.1; 536/23.1, 24.3

(56) References Cited

U.S. PATENT DOCUMENTS

| | | |
|---|---|---|
| 4,810,648 A | 3/1989 | Stalker |
| 5,602,014 A | 2/1997 | Mizummura et al. |
| 5,635,391 A | 6/1997 | Petre et al. |
| 5,858,736 A | 1/1999 | DiCosimo et al. |
| 5,935,840 A * | 8/1999 | Anderson ............... 435/252.3 |
| 6,066,490 A | 5/2000 | Di Cosimo et al. |
| 6,413,768 B1 * | 7/2002 | Galen ..................... 435/320.1 |

FOREIGN PATENT DOCUMENTS

| | | |
|---|---|---|
| CA | 2103616 | 8/1993 |
| WO | WO 01 75077 A2 | 10/2001 |

OTHER PUBLICATIONS http://www.gene-it.com/PDF/GenePASTexperimentV1.pdf, Accessed Dec. 2, 2003.*

Kobayashi, M., *Rhodococcus rhodochrous* aliphatic nitrilase gene, complete cds., XP002194942.

(List continued on next page.)

Primary Examiner—Jeffrey Fredman

(57) ABSTRACT

Recombinant microbial strains are provided that express nitrilase enzyme and are useful as biocatalysts for the hydrolysis of nitrile-containing substrates. The recombinant cells are transformed with a foreign gene isolated from *Acidovorax facilis* 72W encoding a thermostable nitrilase enzyme that catalyzes the hydrolysis of nitrile-containing substrates to carboxylic acids under mild reaction conditions. The nucleotide sequence of the nitrilase gene and the deduced amino acid sequence encoded by the nitrilase gene are provided.

16 Claims, 1 Drawing Sheet

Figure 1:
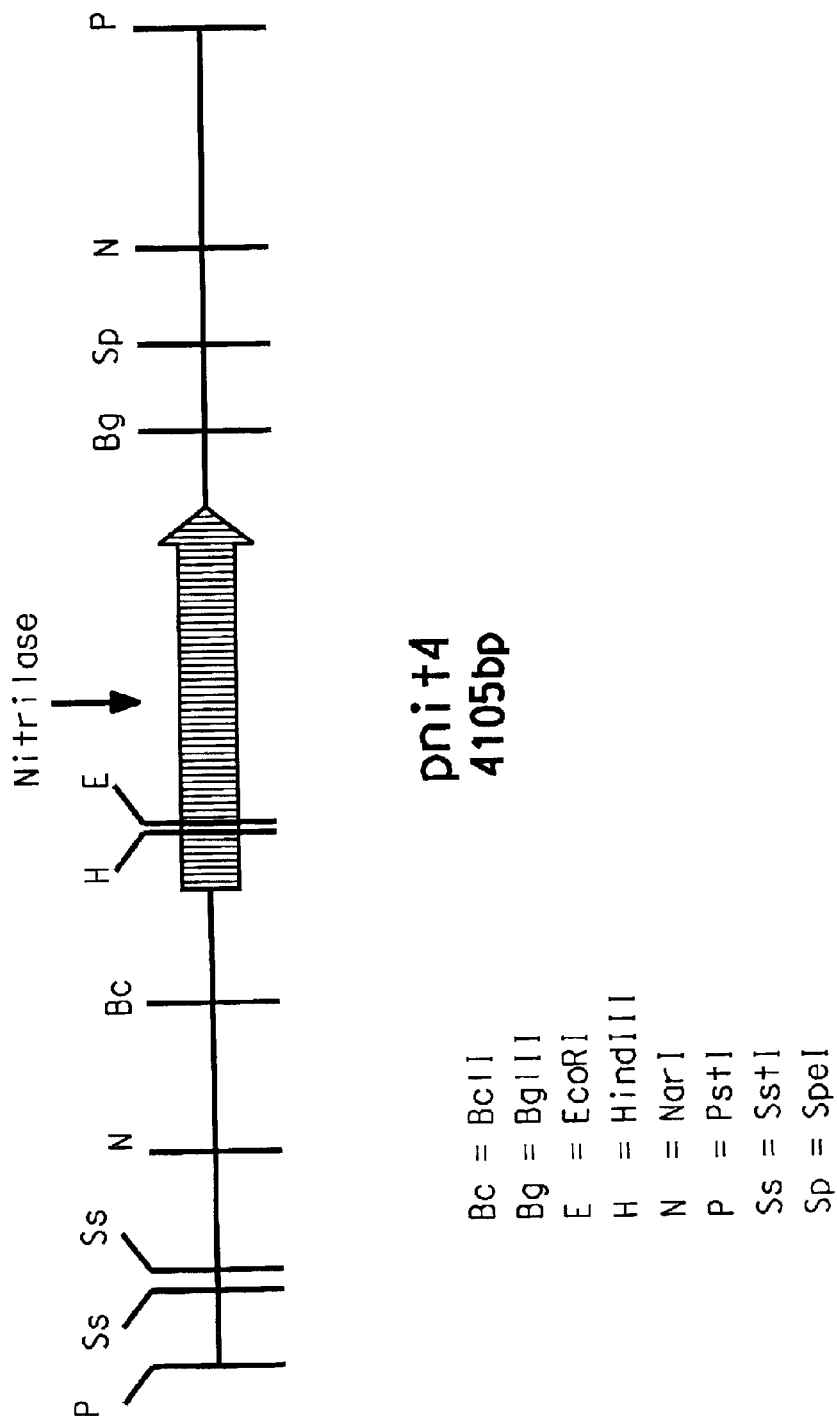

Bc = BclI
Bg = BglII
E = EcoRI
H = HindIII
N = NarI
P = PstI
Ss = SstI
Sp = SpeI

OTHER PUBLICATIONS

Gavagan, J. et al., A Gram–negative Bacterium Producing a Heat–Stable Nitrilase Highly Active on Aliphatic Dinitriles, Applied Microbiology and Biotechnology, Springer Verlag, Berlin, DE, vol. 52, Nov. 1999, pp. 654–659.

Keizou Yamamoto et al: "Purification and Characterization of Nitrilase Responsible for the Enantioselective Hydrolysis from Acinetobacter SP. AK 226", Agricultural and Biological Chemistry, Japan Soc. For Bioscience, biotechnology and Agrochem. Tokyo, JP, vol. 55, No. 6, pp. 1459–1466, Jun. 1, 1991, XP000226135.

Novo et al, *Pseudomanas aeruginosa* Aliphatic Amidase is related to the Nitrilase/Cyanide Hydratase Enzyme Family and CYS 166 is predicted to be the active site necleophile of the catalytic mechanism, Febs Letters, Elsevier Science Publishers, Amsterdam, NL, vol. 367, No. 3, 1995, pp. 275–279, XP000915286.

Almatawah et al., Characterization of an inducible nitrilase from a thermophilic bacillus, Extremophiles, Springer Verlag, Tokyo, JP, vol. 3, No. 4, Nov. 1999, pp. 283–291, XP001062516.

Pace et al., The nitrilase superfamily: classification, structure and function, Genome Biology, vol. 2, No. 1, Jan. 15, 2001, XP001061987.

Kobayashi et al., Primary Structure of an aliphatic Nitrile-Degrading Enzyme, Aliphatic Nitrilase, from *Rhodoccocus rhodochrous* K22 and Expression of its Gene and Identification of its Active Site Residue, Biochemistry, 1992, vol. 31, pp. 9000–9007, XP001062616.

EXTREMOPHILES (1998) 2:207–216.

Kobayashi et al., (Tetrahedron (1990) 46:5587–5590.

Levy–Schil et al., Gene (1995) 161:15–20.

Kobayashi et al., Proc. Nat. Acad. Sci. (1993) 90:247.

Kobayashi et al., J. Biol. Chem. (1992) 267:20746.

Kobayashi et al., Biochem. (1992) 31, 9000.

J. Bacteriology (1990) 172:4807–4815.

Nagasawa et al., Appl. Microbiol. Biotechnol. (1993) 40:189–195.

Cramp et al., Microbiol (1997) 143:2313–2320.

* cited by examiner

SEQUENCE LISTING

<160> NUMBER OF SEQ ID NOS: 32

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Forward primer (1F)
<223> OTHER INFORMATION: K= G or T, M= A or C, S= G or C, Y= C or T

<400> SEQUENCE: 1
tkkmtkccsg gctaycc                                                17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Reverse primer (7R)
<223> OTHER INFORMATION: S= G or C, H= A or C or T, M= A or C, R= A or G, Y= C or T

<400> SEQUENCE: 2
ggccasshtg mrayrtg                                                17

<210> SEQ ID NO 3
<211> LENGTH: 385
<212> TYPE: DNA
<213> ORGANISM: Acidovorax facilis

<400> SEQUENCE: 3
ctattgggcg tggctcggcg acgtgaagta cagcctaagc tttacttcac gctatcacga      60
gaattcgttg gagctaggtg acgaccgtat gcgtcgcctc cagctggccg cgcgccgcaa     120
caaaatcgca ctcgtcatgg gctattcgga gcgggaagcc ggatcgcgct atctgagcca     180
ggtgttcatc gacgagcgtg gcgagatcgt tgccaatcgg cgcaagctga agcccacaca     240
cgttgagcgt acgatctacg gcgaaggcaa cggaaccgat ttcctcacgc acgacttcgc     300

```
gttcggacgc gtcggtggat tgaactgctg ggaacatttc caaccgctca gcaagttcat    360
gatgtacagc ctcggtgagc aggtc                                         385
```

<210> SEQ ID NO 4
<211> LENGTH: 1110
<212> TYPE: DNA
<213> ORGANISM: Acidovorax facilis

<400> SEQUENCE: 4

```
gtggtttcgt ataacagcaa gttcctcgcg gcaaccgttc aggcagagcc ggtatggctc      60
gacgcagacg caacgatcga caagtcgatc ggcatcatcg aagaagctgc ccaaaagggc    120
gcgagtctga tcgctttccc ggaagtattc attccgggct accccctattg gcgtggctc    180 ggcgacgtga agtacagcct aagctttact tcacgctatc acgagaattc gttggagcta    240
ggtgacgacc gtatgcgtcg cctccagctg gccgcgcgcc gcaacaaaat cgcactcgtc    300
atgggctatt cggagcggga agccggatcg cgctatctga gccaggtgtt catcgacgag    360
cgtggcgaga tcgttgccaa tcggcgcaag ctgaagccca cacgttga gcgtacgatc      420 tacggcgaag gcaacggaac cgatttcctc acgcacgact cgcgttcgg acgcgtcggt     480 ggattgaact gctgggaaca tttccaaccg ctcagcaagt tcatgatgta cagcctcggt    540
gagcaggtcc acgttgcatc gtggccggcg atgtccctc ttcagccgga tgttttccaa    600
ctgagcatcg aagccaacgc gacggtcacc cgctcgtacg caatcgaagg ccaaaccttt    660
gtgctttgct cgacgcaggt gatcggacct agcgcgatcg aaacgttctg cctcaacgac    720
gaacagcgcg cactgttgcc gcaaggatgt ggctgggcgc gcatttacgg cccggatgga    780
agcgagcttg cgaagcctct ggcggaagat gctgaggga tcttgtacgc agagatcgat    840
ctggagcaga ttctgctggc gaaggctgga gccgatccgg tcgggcacta ttcgcggcct    900
gacgtgctgt cggtccagtt cgacccgcgc aatcatacgc cagttcatcg catcggcatt    960
gacggtcgct tggatgtgaa tacccgcagt cgcgtggaga atttccgact gcgacaagcg   1020
gctgagcagg agcgtcaggc atccaagcgg ctcggaacga aactctttga caatcccttt   1080
ctggctgaag aaccggtccc agcaaagtag                                    1110
```

<210> SEQ ID NO 5
<211> LENGTH: 369
<212> TYPE: PRT
<213> ORGANISM: Acidovorax facilis

<400> SEQUENCE: 5

```
Val Val Ser Tyr Asn Ser Lys Phe Leu Ala Ala Thr Val Gln Ala Glu
  1               5                  10                  15

Pro Val Trp Leu Asp Ala Asp Ala Thr Ile Asp Lys Ser Ile Gly Ile
             20                  25                  30

Ile Glu Glu Ala Ala Gln Lys Gly Ala Ser Leu Ile Ala Phe Pro Glu
         35                  40                  45

Val Phe Ile Pro Gly Tyr Pro Tyr Trp Ala Trp Leu Gly Asp Val Lys
     50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110
```

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 6
gacgcatatg gtttcgtata acagcaa                                27

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 7
cgacggatcc ttatggctac tttgctgg                               28

<210> SEQ ID NO 8
<211> LENGTH: 31
<212> TYPE: DNA

-continued

<213> ORGANISM: Artificial Sequence
<220> FEATURE:
<223> OTHER INFORMATION: Description of Artificial Sequence:Primer

<400> SEQUENCE: 8
cggatccatg gtttcgtata acagcaagtt c                           31

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 9
ttatggctac tttgctggga ccg                                    23

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
tacatatggt tcgtataac agcaagttc                               29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
catctcgaga tggtttcgta taacag                                 26

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
cactcgagct actttgctgg gac                                    23

<210> SEQ ID NO 13
<211> LENGTH: 1110
<212> TYPE: DNA
<213> ORGANISM: Acidovorax facilis

<400> SEQUENCE: 13
atggtttcgt ataacagcaa gttcctcgcg gcaaccgttc aggcagagcc ggtatggctc      60
gacgcagacg caacgatcga caagtcgatc ggcatcatcg aagaagctgc ccaaaagggc     120
gcgagtctga tcgctttccc ggaagtattc attccgggct accccctattg ggcgtggctc    180 ggcgacgtga agtacagcct aagctttact tcacgctatc acgagaattc gttggagcta    240
ggtgacgacc gtatgcgtcg cctccagctg gccgcgcgcc gcaacaaaat cgcactcgtc    300
atgggctatt cggagcggga agccggatcg cgctatctga gccaggtgtt catcgacgag    360
cgtggcgaga tcgttgccaa tcggcgcaag ctgaagccca cacgttga gcgtacgatc      420 tacggcgaag gcaacggaac cgatttcctc acgcacgact tcgcgttcgg acgcgtcggt    480
ggattgaact gctgggaaca tttccaaccg ctcagcaagt tcatgatgta cagcctcggt      540
gagcaggtcc acgttgcatc gtggccggcg atgtcccctc ttcagccgga tgttttccaa      600
ctgagcatcg aagccaacgc gacggtcacc cgctcgtacg caatcgaagg ccaaaccttt      660
gtgctttgct cgacgcaggt gatcggacct agcgcgatcg aaacgttctg cctcaacgac      720
gaacagcgcg cactgttgcc gcaaggatgt ggctgggcgc gcatttacgg cccggatgga      780
agcgagcttg cgaagcctct ggcggaagat gctgagggga tcttgtacgc agagatcgat      840
ctggagcaga ttctgctggc gaaggctgga gccgatccgg tcgggcacta ttcgcggcct      900
gacgtgctgt cggtccagtt cgacccgcgc aatcatacgc agttcatcg catcggcatt      960 gacggtcgct tggatgtgaa tacccgcagt cgcgtggaga atttccgact gcgacaagcg     1020
gctgagcagg agcgtcaggc atccaagcgg ctcggaacga aactctttga acaatccctt     1080
ctggctgaag aaccggtccc agcaaagtag                                      1110

<210> SEQ ID NO 14
<211> LENGTH: 369
<212> TYPE: PRT
<213> ORGANISM: Acidovorax facilis

<400> SEQUENCE: 14

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

-continued

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 15
<211> LENGTH: 1776
<212> TYPE: DNA
<213> ORGANISM: Acidovorax delafieldii

<400> SEQUENCE: 15

| | | |
|---|---|---|
| tgatcactcc tgaccacctt gctgaaaaat tcagcagcgt agccgtcaac gtggctcaat | 60 |
| tttcagtgtg atccacccca aaatggccc agttttcgtt gtgattcaac agcgtcgtgt | 120 |
| ctatgacgtc tactccatac tttcgcaaga aaaggggggg gaaattttttc attcccaat | 180 |
| tattagggag atcggtctaa tagtaaaggg caaaccctga ttttttatta ggctagatgg | 240 |
| tctaataatt aaatcagctc ggcgaatgcg tagcgctcgg gcaacccaga caaggcaatt | 300 |
| ctgacagtga caccctctt aggagacgac cgtggtttcg tataacagca agttcctcgc | 360 |
| ggcaaccgtt caggcagagc cggtatggct cgacgcagac gcaacgatcg acaagtcgat | 420 |
| cggcatcatc gaagaagctg cccaaaaggg cgcgagtctg atcgctttcc cggaagtatt | 480 |
| cattccgggc taccctatt gggcgtggct cggcgacgtg aagtacagcc taagctttac | 540 |
| ttcacgctat cacgagaatt cgttggagct aggtgacgac cgtatgcgtc gcctccagct | 600 |
| ggccgcgcgc cgcaacaaaa tcgcactcgt catgggctat tcggagcggg aagccggatc | 660 |
| gcgctatctg agccaggtgt tcatcgacga gcgtggcgag atcgttgcca atcggcgcaa | 720 |
| gctgaagccc acacacgttg agcgtacgat ctacggcgaa gcaacggaa ccgatttcct | 780 |
| cacgcacgac ttcgcgttcg gacgcgtcgg tggattgaac tgctgggaac atttccaacc | 840 |
| gctcagcaag ttcatgatgt acagcctcgg tgagcaggtc cacgttgcat cgtggccggc | 900 |
| gatgtcccct cttcagccgg atgttttcca actgagcatc gaagccaacg cgacggtcac | 960 |
| ccgctcgtac gcaatcgaag gccaaaacctt tgtgctttgc tcgacgcagg tgatcggacc | 1020 |
| tagcgcgatc gaaacgttct gcctcaacga cgaacagcgc gcactgttgc cgcaaggatg | 1080 |
| tggctgggcg cgcatttacg gcccggatgg aagcgagctt gcgaagcctc tggcggaaga | 1140 |
| tgctgagggg atcttgtacg cagagatcga tctggagcag attctgctgg cgaaggctgg | 1200 |
| agccgatccg gtcgggcact attcgcggcc tgacgtgctg tcggtccagt tcgacccgcg | 1260 |
| caatcatacg ccagttcatc gcatcggcat tgacggtcgc ttggatgtga ataccccgcag | 1320 |
| tcgcgtggag aatttccgac tgcgacaagc ggctgagcag gagcgtcagg catccaagcg | 1380 |
| gctcggaacg aaactctttg aacaatccct tctggctgaa gaaccggtcc cagcaaagta | 1440 |

```
gccataagtt gagagtcgcg agatagtatc ggggaaagcc atctctggtc ttcccctta       1500 ttctccaagc cgacatcacc gctgaaagcg ggtttctttg ctaccccgag tttcgatccc      1560
gcatcgccgt cgcgtgagat ttgcgtcaga gcggacattc aagttgtgtg gcaaggtcgt      1620
ccagactgtc cacggaaaat tcccagttct cactcggttc aaggtcagtc gtttgctgcg      1680
ggccgtgttc ctgtggccgc ctgacgaatg ccgtcctcag ccacaacgt cgagcggctg       1740 ccaagtcatc gttgtgcgcc gccaccatgc agatct                                1776
```

<210> SEQ ID NO 16
<211> LENGTH: 1110
<212> TYPE: DNA
<213> ORGANISM: Artificial Sequence
<220> FEATURE:
<223> OTHER INFORMATION: Description of Artificial Sequence: A synthetic version of the nitrilase gene

<400> SEQUENCE: 16

```
atggtttctt acaactccaa gttcttggct gctactgttc aagctgagcc agtttggttg       60
gacgcagacg ctactattga caagtctatc ggtatcatcg aagaagctgc caaaagggt       120 gcctctttga tcgctttccc agaagttttc attccaggtt acccatactg ggcctggttg      180
ggtgacgtta agtactcttt gtcctttact tccagatatc acgagaactc tttggagttg      240
ggtgacgaca gaatgcgtag actgcaattg gctgcccgta gaaacaaaat tgctttggtc      300
atgggttatt ccgagagaga agctggatct cgttacttgt cccaagtctt catcgacgag      360
agaggtgaga ttgttgcaaa tcgtcgtaag ttgaagccaa ctcacgttga gcgtaccatc      420 tacgagaag gtaacggaac cgatttcttg actcacgact tcgccttcgg aagagttggt      480
ggattgaact gttgggaaca tttccaacct ctgtctaagt tcatgatgta ctccttgggt      540
gagcaagtcc acgttgcttc ttggccagct atgtcccctc ttcagccaga tgttttccaa      600
ttgtccatcg aagccaacgc caccgtcacc agatcctacg ccatcgaagg tcaaactttt      660
gtcctttgct ctacccaggt cattggacct tctgctatcg aaaccttctg tctgaacgac      720
gaacagagag ctttgttgcc acaaggatgt ggttgggcaa gaatttacgg tccagatgga      780
tctgagcttg ccaagccttt ggctgaagat gctgagggta ttttgtacgc tgagatcgat      840
ttggagcaaa ttctgctggc caaggctgga gccgatccag tcggtcacta ctccagacct      900
gacgtcttgt ccgtccagtt cgaccctaga accacactc cagttcacag aattggtatt       960
gacggtagat tggatgttaa caccagatcc agagtcgaga acttcagact gagacaagct      1020
gctgagcagg agagacaggc ttctaagaga cttggaacta aacttttcga caatctctt       1080 ttggctgaag aacctgtccc agccaagtaa                                        1110
```

<210> SEQ ID NO 17
<211> LENGTH: 84
<212> TYPE: DNA
<213> ORGANISM: Artificial Sequence
<220> FEATURE:
<223> OTHER INFORMATION: Description of Artificial Sequence:Synthetic oligonucleotide

<400> SEQUENCE: 17

```
catgaattca tggtttctta caactccaag ttcttggctg ctactgttca agctgagcca       60
gtttggttgg acgcagacgc tact                                              84
```

<210> SEQ ID NO 18
<211> LENGTH: 90

<212> TYPE: DNA
<213> ORGANISM: Artificial Sequence
<220> FEATURE:
<223> OTHER INFORMATION: Description of Artificial Sequence:Synthetic
oligonucleotide

<400> SEQUENCE: 18
tttgatcgct ttcccagaag ttttcattcc aggttaccca tactgggcct ggttgggtga    60
cgttaagtac tctttgtcct ttacttccag                                    90

<210> SEQ ID NO 19
<211> LENGTH: 90
<212> TYPE: DNA
<213> ORGANISM: Artificial Sequence
<220> FEATURE:
<223> OTHER INFORMATION: Description of Artificial Sequence:Synthetic
oligonucleotide

<400> SEQUENCE: 19
aattggctgc ccgtagaaac aaaattgctt tggtcatggg ttattccgag agagaagctg    60
gatctcgtta cttgtcccaa gtcttcatcg                                    90

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence:Synthetic
Oligonucleotide

<400> SEQUENCE: 20
gttgagcgta ccatctacgg agaaggtaac ggaaccgatt tcttgactca cgacttcgcc    60
ttcggaagag ttggtggatt gaactgttgg                                    90

<210> SEQ ID NO 21
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
agtccacgtt gcttcttggc cagctatgtc ccctcttcag ccagatgttt tccaattgtc    60
catcgaagcc aacgccaccg tcaccagatc                                    90

<210> SEQ ID NO 22
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
gaccttctgc tatcgaaacc ttctgtctga acgacgaaca gagagctttg ttgccacaag    60
gatgtggttg ggcaagaatt tacggtccag                                    90

<210> SEQ ID NO 23
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tacgctgaga tcgatttgga gcaaattctg ctggccaagg ctggagccga tccagtcggt    60
cactactcca gacctgacgt cttgtccgtc    90

<210> SEQ ID NO 24
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tagattggat gttaacacca gatccagagt cgagaacttc agactgagac aagctgctga    60
gcaggagaga caggcttcta agagacttgg    90

<210> SEQ ID NO 25
<211> LENGTH: 84
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 25
catgaattct tacttggctg ggacaggttc ttcagccaaa agagattgtt cgaaaagttt    60
agttccaagt ctcttagaag cctg    84

<210> SEQ ID NO 26
<211> LENGTH: 90
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 26
tggtgttaac atccaatcta ccgtcaatac caattctgtg aactggagtg tggtttctag    60
ggtcgaactg gacggacaag acgtcaggtc    90

<210> SEQ ID NO 27
<211> LENGTH: 90
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 27
tccaaatcga tctcagcgta caaaataccc tcagcatctt cagccaaagg cttggcaagc    60
tcagatccat ctggaccgta aattcttgcc    90

<210> SEQ ID NO 28
<211> LENGTH: 90
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 28

-continued

```
ggtttcgata gcagaaggtc caatgacctg ggtagagcaa aggacaaaag tttgaccttc      60
gatggcgtag gatctggtga cggtggcgtt                                      90

<210> SEQ ID NO 29
<211> LENGTH: 90
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 29
gccaagaagc aacgtggact tgctcaccca aggagtacat catgaactta gacagaggtt     60
ggaaatgttc ccaacagttc aatccaccaa                                      90

<210> SEQ ID NO 30
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccgtagatgg tacgctcaac gtgagttggc ttcaacttac gacgatttgc aacaatctca     60
cctctctcgt cgatgaagac ttgggacaag                                      90

<210> SEQ ID NO 31
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtttctacgg gcagccaatt gcagtctacg cattctgtcg tcacccaact ccaaagagtt     60
ctcgtgatat ctggaagtaa aggacaaaga                                      90

<210> SEQ ID NO 32
<211> LENGTH: 90
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 32
cttctgggaa agcgatcaaa gaggcaccct tttgggcagc ttcttcgatg ataccgatag     60
acttgtcaat agtagcgtct gcgtccaacc                                      90
```

ISOLATION AND EXPRESSION OF A GENE FOR A NITRILASE FROM *ACIDOVORAX FACILIS* 72W

This application claims benefit of Ser. No. 60/193,707 filed on Mar. 31, 2000.

FIELD OF INVENTION

The present invention relates to the field of molecular biology and the use of recombinant microorganisms to express desired genes and gene products. More specifically, the gene used in the invention is a novel nucleic acid fragment encoding a nitrilase enzyme that catalyzes the hydrolysis of a wide variety of nitrile-containing substances to produce a corresponding carboxylic acid. Also provided are recombinant strains that express nitrilase activity and are useful as biocatalysts for the hydrolysis of nitrile-containing substrates. Additionally, the invention relates to specific nucleic acids that aid in isolating such nitrilase genes.

BACKGROUND

Nitriles are readily converted to the corresponding carboxylic acids by a variety of chemical processes, but these processes typically require strongly acidic or basic reaction conditions and high reaction temperatures, and usually produce unwanted byproducts and/or large amounts of inorganic salts as unwanted waste. Processes in which enzyme-catalyzed hydrolysis converts nitrile-containing substrates to the corresponding carboxylic acids are often preferred to chemical methods because these processes 1) are often run at ambient temperature, 2) do not require the use of strongly acidic or basic reaction conditions, and 3) do not produce large amounts of unwanted byproducts. Especially advantageous over chemical hydrolysis, the enzyme-catalyzed hydrolysis of a variety of aliphatic or aromatic dinitriles can be highly regioselective, where only one of the two nitrile groups is hydrolyzed to the corresponding carboxylic acid ammonium salt.

Enzyme-catalyzed hydrolysis of nitrile substrates to the corresponding carboxylic acids may be accomplished via a one- or two-step reaction (Table 1).

TABLE 1

|  | Substrates* | Product(s) | Enzyme |
|---|---|---|---|
| Two Step | | | |
| Reaction 1 | RCN + H$_2$O | RC(O)NH$_2$ | nitrile hydratase |
| Reaction 2 | RC(O)NH$_2$ + H$_2$O | RC(O)OH + NH$_3$ | amidase |
| One Step | | | |
| Reaction 1 | RCN + 2H$_2$O | RC(O)OH + NH$_3$ | nitrilase |

*R represents a varying spectrum of organic substituents particular to a chosen enzyme.

A wide variety of bacterial genera collectively possess a diverse spectrum of nitrile hydratase, amidase, or nitrilase activities, including *Rhodococcus, Pseudomonas, Alcaligenes, Arthrobacter, Bacillus, Bacteridium, Brevibacterium, Corynebacterium, Agrobacterium, Micrococcus*, and *Comamonas*. Both aqueous suspensions of these microorganisms and the isolated enzymes have been used to convert nitriles to carboxylic acids. Biotechnological use of these enzymes has been recently reviewed by Cowan et al. (*Extremophiles* (1998) 2:207–216).

A nitrilase enzyme directly converts a nitrile to the corresponding carboxylic acid in aqueous solution without the intermediate formation of an amide. The use of nitrilases for the hydrolysis of aromatic nitrites to the corresponding carboxylic acid ammonium salts has been known for many years, but it is only recently that the use of nitrilases to convert aliphatic nitriles has been reported. Kobayashi et al. (*Tetrahedron* (1990) 46:5587–5590; *J. Bacteriology* (1990) 172:4807–4815) have described an aliphatic nitrilase isolated from *Rhodococcus rhodochrous* K22 which catalyzed the hydrolysis of aliphatic nitriles to the corresponding carboxylic acid ammonium salts; several aliphatic α,ω-dinitriles were also hydrolyzed. A nitrilase from *Comamonas testosteroni* has been isolated which can convert a range of aliphatic α,ω-dinitriles to either the corresponding ω-cyanocarboxylic acid ammonium salt or the dicarboxylic acid diammonium salt (CA 2,103,616; and Lévy-Schil et al., *Gene* (1995) 161:15–20).

The nitrilase activity of unimmobilized *Acidovorax facilis* 72W cells has been used in a process to prepare five-membered or six-membered ring lactams from aliphatic α,ω-dinitriles (U.S. Pat. No. 5,858,736). In that process, an aliphatic α,ω-dinitrile is first converted to an ammonium salt of an ω-cyanocarboxylic acid in aqueous solution using a catalyst having an aliphatic nitrilase (EC 3.5.5.7) activity. The ammonium salt of the ω-cyanocarboxylic acid is then converted directly to the corresponding lactam by hydrogenation in aqueous solution, without isolation of the intermediate ω-cyanocarboxylic acid or ω-aminocarboxylic acid. When the aliphatic α,ω-dinitrile is also unsymmetrically substituted at the α-carbon atom, the nitrilase produces the ω-cyanocarboxylic acid ammonium salt resulting from hydrolysis of the ω-nitrile group with greater than 98% regioselectivity, thereby producing only one of the two possible lactam products during the subsequent hydrogenation. For example, 2-methylglutaronitrile (MGN) was hydrolyzed by unimmobilized *Acidovorax facilis* 72W cells to produce 4-cyanopentanoic acid (4-CPA) ammonium salt with greater than 98% regioselectivity at 100% conversion.

Nitrilase genes have been cloned and expressed in heterologous systems, especially in *Escherichia coli*. Petre et al. (U.S. Pat. No. 5,635,391) disclose expression of a nitrilase from *Comamonas testosteroni* in *E. coli* and *Pseudomonas putida*. Also disclosed is a method to improve levels of soluble nitrilase protein in *E. coli* by coexpression of the GroE chaperonin protein, which results in higher nitrilase specific activity. The *E. coli* promoters P$_{lac}$ and P$_{trp}$ were used to drive expression of the nitrilase coding sequences. In *E. coli* P$_{lac}$ has also been used successfully in expressing nitrilase coding sequences from *Alcaligenes faecalis* JM3 (Kobayashi et al., *Proc. Nat. Acad. Sci.* (1993) 90:247 and JP #4-30663), *Rhodococcus rhodochrous* J3 (Kobayashi et al., *J. Biol. Chem.* (1992) 267:20746) and *Rhodococcus rhodochrous* K22 (Kobayashi et al., *Biochem.* (1992) 31, 9000). Stalker (U.S. Pat. No. 4,810,648) discloses that the gene for a haloarylnitrile-hydrolyzing nitrilase can be expressed under control of its native promoter in *E. coli*. In U.S. Pat. No. 5,602,014, Mizumura and Yu disclose a specialized regulatory system for expression of nitrilase genes in *Rhodococcus erythropolis*.

Nitrilase enzymes are reported to be highly labile and not obtainable in large quantities (Kobayashi et al., *Tetrahedron* (1990) 46:5587–5590; *J. Bacteriology* (1990) 172:4807–4815). In contrast to nitrile hydratase, nitrilases are characterized by low specific activities and reaction rates (Nagasawa et al., *Appl Microbiol. Biotechnol.* (1993) 40:189–195). The inherent thermal instability of nitrile-hydrolyzing enzymes from mesophiles is reported to limit their industrial applications (Cramp et al., *Microbiol.* (1997) 143:2313–2320).

The problem remains the lack of an industrially useful, thermostable, and highly productive nitrilase enzyme suitable as a catalyst for nitrile-containing substrates in applications (such as the regioselective hydrolysis of aliphatic dinitriles to cyanocarboxylic acids) where high yields of product are obtained under mild reaction conditions (including ambient temperatures and without extreme acidic or basic conditions) and without generating relatively large amounts of undesirable wastes.

SUMMARY OF THE INVENTION

The instant invention provides for an isolated DNA sequence specific to the *Acidovorax* 72W nitrilase gene. The instant invention includes isolated nucleic acid fragments that are complementary to the complete sequences of the accompanying Sequence Listing as well as substantially similar nucleic acid sequences. The instant invention includes any nucleic acid fragment that encodes all or a substantial portion of the amino acid sequence of the nitrilase enzyme as set forth in SEQ ID NO:5 or SEQ ID NO:14. The invention also includes an isolated nucleic acid molecule that hybridizes with the nucleic acid fragment encoding all or a substantial portion of the amino acid sequences of SEQ ID NO:5 or SEQ ID NO:14 under hybridization conditions of 6×SSC (1M NaCl), 40–45% formamide, 1% SDS at 37° C., and a wash in 0.5× to 1×SSC at 55 to 60° C. Nucleic acid fragments complementary to the listed SEQ ID NOs:1–16 are also claimed. Polypeptides encoded by the nucleic acid fragments of the invention are also provided, for example, SEQ ID NO:5 and SEQ ID NO:14. The invention includes RNA or antisense RNA molecules transcribed from sequences described above and their cDNA derivatives.

Also provided are methods to produce active enzyme protein from these nitrilase coding sequences in transformed microorganisms. The improvement obtained from this invention is an increased reaction rate and higher reactor productivity due to the increased specific activity of the transformant catalysts relative to *Acidovorax facilis* 72W. The active nitrilase enzyme produced in whole cells transformed with genetic materials described herein can be used to carry out useful hydrolysis of nitrile-containing substrates. Transformed microorganisms containing expression cassettes comprising chimeric genes having plasmids containing the isolated nucleic acid fragment encoding nitrilase enzyme, each unit as described herein, are also part of this invention. One embodiment uses any of the specific enzyme catalysts *E. coli* SW91 (ATTC PTA-1175), *E. coli* DH5α:pnit4 (ATTC PTA-1176), *E. coli* SS1001 (ATTC PTA-1177), *E. coli* SS1002 containing plasmid pnitex2, or *E. coli* SS1011 containing plasmid pnitex2 in contact with α,ω-cyanocarboxylic acid. A further embodiment uses the specific transformed microorganisms in an improved method to convert α,ω-dinitriles to ω-cyanocarboxylic acids, which are intermediate in the preparation of five-membered or six-membered ring lactams (See U.S. Pat. No. 5,858,736).

A method is provided for using a native microbial gene, specifically from *Acidorovax facilis* 72W, encoding a protein characterized by a nitrilase activity on nitrile-containing substrates to obtain a mutated microbial gene encoding a protein characterized by an increased specific nitrilase activity on nitrile-containing substrates and/or increased stability of the nitrilase, one or both characteristics increased relative to that of the native microbial gene, the mutated microbial gene produced by a method comprising the steps of
 (i) contacting restriction endonucleases with a mixture of nucleotide sequences to yield a mixture of restriction fragments, the mixture of nucleotide sequences comprising
   a) a native microbial gene;
   b) a first population of nucleotide fragments which will hybridize with the nucleotide sequences of the native microbial gene of (i)(a); and
   c) a second population of nucleotide fragments which will not hybridize to the nucleotide sequences of the native microbial gene of (i)(a),
 (ii) denaturing the mixture of restriction fragments of step (i);
 (iii) incubating the denatured mixture of restriction fragments of step (ii) with a polymerase; and
 (iv) repeating steps (ii) and (iii) a sufficient number of times to yield
a mutated microbial gene encoding a protein characterized by an increased specific nitrilase activity on nitrile-containing substrates and/or increased stability of the nitrilase, on or both characteristics increased relative to that of the native microbial gene. The invention includes mutated microbial genes produced by this method.

BRIEF DESCRIPTION OF THE FIGURES, BIOLOGICAL DEPOSITS, AND SEQUENCE LISTING

The invention can be more fully understood from the figure, the biological deposits, the accompanying sequence descriptions, the detailed description, and claims which together constitute this application.

FIG. 1 shows a restriction map of the 4.1 kb PstI fragment of pnit4. The BclI-BglII fragment contains the nitrilase gene and the flanking chromosomal region.

Applicants have made the following biological deposits under the terms of the Budapest Treaty on the International Recognition of the Deposit of Micro-organisms for the purposes of Patent Procedure:

| Depositor Identification Reference | International Depository Designation | Date of Deposit |
|---|---|---|
| *E. coli* SW91 | ATCC PTA-1175 | 11 Jan. 2000 |
| *E. coli* DH5α: pnit4 | ATCC PTA-1176 | 11 Jan. 2000 |
| *E. coli* SS1001 | ATCC PTA-1177 | 11 Jan. 2000 |

As used herein, "ATCC" refers to the American Type Culture Collection International Depository Authority located at ATCC, 10801 University Blvd., Manassas, Va. 20110-2209, USA. The "International Depository Designation" is the accession number of the culture on deposit with ATCC.

The listed deposit(s) will be maintained in the indicated international depository for at least thirty (30) years and will be made available to the public upon the grant of a patent disclosing it. The availability of a deposit does not constitute a license to practice the subject invention in derogation of patent rights granted by government action.

Applicant(s) have provided 32 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of a forward primer (1F) which was derived from a conserved region found in bacterial nitrilase sequences available from GenBank data and was used as degenerate PCR primers to discover a novel nitrilase gene.

SEQ ID NO:2 is the nucleotide sequence of a reverse primer (7R) which was derived from a conserved region found in bacterial nitrilase sequences available from GenBank data and was used as degenerate PCR primers to discover a novel nitrilase gene.

SEQ ID NO:3 is the nucleotide sequence of the *Acidovorax facilis* 72W genomic portion of the pJJ28–5 clone without degenerate primer regions.

SEQ ID NO:4 is the nucleotide sequence of the *Acidovorax facilis* 72W nitrilase coding sequence identified within the 4.1 kb insert from pnit4.

SEQ ID NO:5 is the amino acid sequence deduced from the nucleotide sequence (SEQ ID NO:4, SEQ ID NO:15) encoded by *Acidovorax facilis* 72W nitrilase coding sequence.

SEQ ID NO:6 is the nucleotide sequence of a forward primer which was used to amplify the nitrilase coding sequence from *Acidovorax facilis* 72W genomic DNA.

SEQ ID NO:7 is the nucleotide sequence of a reverse primer which was used to amplify the nitrilase coding sequence from *Acidovorax facilis* 72W genomic DNA.

SEQ ID NO:8 is the nucleotide sequence of a forward primer which was used to amplify the nitrilase coding sequence from *Acidovorax facilis* 72W genomic DNA.

SEQ ID NO:9 is the nucleotide sequence of a reverse primer which was used to amplify the nitrilase coding sequence from *Acidovorax facilis* 72W genomic DNA.

SEQ ID NO:10 is the nucleotide sequence of a forward primer which was used to amplify the nitrilase coding sequence from *Acidovorax facilis* 72W genomic DNA.

SEQ ID NO:11 is the nucleotide sequence of a forward primer which was used to amplify the nitrilase coding sequence from *Acidovorax facilis* 72W genomic DNA and which was also used to incorporate XhoI restriction sites.

SEQ ID NO:12 is the nucleotide sequence of a reverse primer used to amply the nitrilase coding sequence from *Acidovorax facilis* 72W genomic DNA and which was used to incorporate XhoI restriction sites.

SEQ ID NO:13 is the nucleotide sequence of the nitrilase coding sequence in plasmid pnitex2 used for overexpression in *E. coli*.

SEQ ID NO:14 is the deduced amino acid sequence encoded by the nitrilase coding sequence in plasmid pnitex2 used for overexpression of nitrilase enzyme in *E. coli*.

SEQ ID NO:15 is the nucleotide sequence of a 1776 bp BclI-BglII genomic fragment of the plasmid pnit4 containing nitrilase gene and flanking chromosomal region from *Acidovorax facilis* 72W.

SEQ ID NO:16 is a synthetic version of the nitrilase gene, with codon usage optimized for expression in *Pichia*.

SEQ ID NOs:17–32 are oligonucleotides used to construct the synthetic nitrilase gene of SEQ ID NO:16.

DETAILED DESCRIPTION OF THE INVENTION

Applicants have solved the stated problem with an invention relating to the use of a nitrilase gene sequence encoding a protein useful as a biocatalyst for the hydrolysis of nitrile-containing substrates to a carboxylic acid. The product of nitrile hydrolysis, a carboxylic acid, may also be in the form of a carboxylic acid salt with byproducts of ammonia or other buffer components. The nitrilase gene was isolated from *Acidovorax facilis* 72W. Specifically, recombinant strains of host cells (such as *E. coli*) that express active *Acidovorax facilis* 72W nitrilase protein are extremely useful to catalyze the hydrolysis of a wide variety of nitrile-containing substrates, including the highly regioselective hydrolysis of dinitriles. Typical dinitriles will have the formula NC—R—CN where R is an alkylene group having from about 1 to about 10 carbons.

This biocatalytic process is industrially attractive as it generates much smaller quantities of undesirable wastes and operates under much milder conditions than previously known methods. The products of the present invention are useful as precursors for polymers, solvents, and chemicals of high value in the chemical, agricultural, and pharmaceutical industries.

Applicants' solution to the problems existing in the technical field arose out of the following accomplishments which are discussed in more detail below and in the Examples:

I. provided degenerate PCR primer sequences (SEQ ID NOs:1 and 2) useful for identifying the presence of unknown nitrilase genes in bacteria;

II. isolated nucleic acid sequences useful in screening for the presence of any nitrilase gene;

III. mapped, identified, and cloned the complete coding sequence for a regioselective, thermostable nitrilase from *Acidovorax facilis* 72W (ATCC 55746) (SEQ ID NO:4 and 15);

IV. constructed recombinant DNA plasmids pSW91, pnit4, and pnitex2, chimeric genes, and expression cassettes containing the coding sequence as described in III located within a 4.1 kb chromosomal DNA fragment from *Acidovorax facilis* 72W (ATCC 55746);

V. constructed recombinant strains of *E. coli* that express active *Acidovorax facilis* 72W nitrilase protein;

VI. demonstrated regioselective hydrolysis of 2-methylglutaronitrile (MGN) to 4-cyanopentanoic acid (4-CPA) using whole cells of the recombinant *E. coli* expressing the *Acidovorax facilis* 72W nitrilase protein described herein; and teach the use of a native microbial gene encoding a protein characterized by a nitrilase activity on nitrile-containing substrates (preferably 2-methylglutaronitrile) to obtain a mutated microbial gene encoding a protein characterized by altered nitrilase activity and/or greater stability, one or both characteristic increased relative to that of the native nitrilase protein.

*Acidovorax facilis* 72W nitrilase proved to be an unexpectedly robust catalyst for producing carboxylic acids from aliphatic or aromatic nitrites. All known nitrilases, including *Acidovorax facilis* 72W nitrilase, have a nucleophilic cysteine in the enzyme active site (Cowan et al., (1998) supra) and all are susceptible to inactivation by thiol reagents (1.0 mM concentrations of copper chloride, silver nitrate, mercuric acetate, or ferric chloride each produced major decreases in 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *Acidovorax facilis* 72W cells used as a catalyst produced up to $3.9 \times 10^7$ moles of product (4-CPA) per mole of nitrilase enzyme (total turnover number, TTN).

The expression of active *Acidovorax facilis* 72W nitrilase in a heterologous host cell has several additional advantages over the preparation and use of *Acidovorax facilis* 72W cells as a nitrilase catalyst. The level of expression of the nitrilase protein in *Acidovorax facilis* 72W is ca. 3.4% of total soluble protein (Example 14) and is constitutive; a thorough screening of potential inducers of nitrilase production (aliphatic or aromatic nitriles or amides, lactams, ureas, etc.) found no effect on the level of nitrilase produced during fermentation of *Acidovorax facilis* 72W.

In contrast, *E. coli* transformants expressed enzymatically-active *Acidovorax facilis* 72W nitrilase at levels of up to 12% of total soluble protein; the total amount of nitrilase produced (active and inactive) in *E. coli* transformants was as high as 58% of total soluble protein. This increased level of nitrilase expression in *E. coli* transformant cells results in up to a 2.4-fold increase in specific activity (units of nitrilase activity per gram dry cell weight) relative to *Acidovorax facilis* 72W cells, which in turn significantly increases the catalyst productivity (g product produced/g dry cell weight/h) (Examples 7 and 9). Moreover, *Acidovorax facilis* 72W cells require glycerol, a relatively expensive carbon substrate, when grown by fermentation, and have not been successfully grown using inexpensive glucose. In contrast, *E. coli* transformants can be grown on glucose to the same cell density as *Acidovorax facilis* 72W cells in about half the time, significantly reducing biocatalyst production costs.

*Acidovorax facilis* 72W cells additionally contain a nitrile hydratase and an 1amidase, neither of which are regioselective, and which can produce unwanted byproducts when converting α,ω-dinitriles to the corresponding ω-cyanocarboxylic acid ammonium salts. *Acidovorax facilis* 72W cells required heat-treatment to inactivate the nitrile hydratase and amidase enzymes (U.S. Pat. No. 5,814,508), risking loss of nitrilase activity and adding production costs. *Acidovorax facilis* mutant strains 72-PF-15 and 72-PF-17 were prepared which lacked the nitrile hydratase enzyme (U.S. Pat. No. 5,858,736), but these strains had only ca. half the nitrilase specific activity of the parent *Acidovorax facilis* 72W strain.

In contrast, an *E. coli* transformed with the genetic material to express nitrilase enzyme does not require a heat-treatment step to inactivate unwanted nitrile hydratase or amidase activities, eliminating the cost of this processing step for catalyst production and avoiding the inadvertent loss of nitrilase activity. *E. coli* transformants having a high specific nitrilase activity with the attendant advantages have been produced by Applicants as described in Examples 6 and 7.

The whole-cell nitrilase activity of *Acidovorax facilis* 72W is very stable at temperatures of up to about 55° C.; a cell suspension in 0.10 M phosphate buffer (pH 7.0) had a nitrilase half-life of 22.7 h at 50° C. (Gavagan et al., *Appl. Microbiol. Biotechnol.* (1999) 52:654–659). The purified enzyme also had excellent temperature stability, where no loss of activity of a 10 mg/mL solution of purified nitrilase in 0.10 M phosphate buffer was observed after 24 h at 45° C. When stored as a solution in 50 mM potassium phosphate buffer (pH 7.0) at 5° C., no loss of activity of purified nitrilase was observed after 46 days. Although *Acidovorax facilis* 72W, a mesophilic bacterium, has an optimal temperature for growth of 32° C., the 72W nitrilase enzyme itself has a thermal stability that compares favorably to the nitrilase enzyme of a thermophilic bacterium such as the *Bacillus pallidus* strain DAC521 (Cramp et al., *Microbiol.* (1997) 13:2313–2320).

When unimmobilized cells are used as a catalyst for hydrolysis of MGN to 4-CPA, either centrifugation or ultrafiltration was required to recover the unimmobilized cells for reuse. At high product concentrations (up to 29 wt. % 4-CPA ammonium salt), the unimmobilized cells lost significant activity with each reuse and cell lysis was observed. In contrast, immobilizing the cells simplified catalyst recovery and reuse, improved the resistance of cells to lysis, and increased the stability of the enzyme activity of the immobilized cells when recycled in consecutive batch reactions as compared to using unimmobilized cells.

Immobilization of either whole cell *Acidovorax facilis* 72W or the *E. coli* transformant SS1001 in carrageenan under identical conditions produced gels that were stable when recycled in consecutive batch reactions which produced high concentrations of 4-CPA ammonium salt (up to ca. 200 g/L). Gel beads were prepared by first dispersing a heated aqueous suspension of cells (5% dry cell weight) and carrageenan (3 wt %) in heated soybean oil at 50° C., and the resulting droplets were gelled by lowering the temperature of the oil below the gelling temperature of the carrageenan (Audet et al., *Process Biochem.* (1989) 24:217). The cell/carrageenan beads, which had an average diameter of from 0.5 mm–3 mm, were separated from the soybean oil, then washed with aqueous buffer and crosslinked with glutaraldehyde and polyethyleneimine.

*Acidovorax facilis* 72W cells and the *E. coli* transformant SS1001 cells immobilized in carrageenan beads were compared in side-by-side reactions under identical conditions for the production of 1.25 M 4-CPA ammonium salt. The reaction rate when using immobilized *E. coli* transformant SS1001 was 1.7 times greater than when using immobilized *Acidovorax facilis* 72W cells (310 mM 4-CPA ammonium salt/h and 184 mM 4-CPA ammonium salt/h, respectively; Example 9). The increase in reaction rate obtained with *E. coli* transformant SS1001 was a result of the higher specific activity (units of nitrilase activity per gram of beads) of the immobilized transformant cell catalyst, and demonstrates one advantage of using a transformant cell with higher specific nitrilase activity relative to the parent *Acidovorax facilis* 72W strain. The reaction rate when using *E. coli* transformant SW91 cells immobilized in calcium alginate beads according to a published procedure (Bucke, *Methods Enzymol.* (1987) 135:175–189) was 4.0 times greater than when using carrageenan-immobilized *Acidovorax facilis* 72W cells (739 mM 4-CPA ammonium salt/h and 184 mM 4-CPA ammonium salt/h, respectively; Examples 9 and 11). The increased catalyst productivity (g product/g catalyst/h) achieved by using the immobilized transformant catalyst significantly reduces process costs.

The invention provides a new nucleic acid sequence encoding nitrilase enzyme. This sequence comprises an open reading frame (ORF) residing on a 4.1 kb PstI fragment isolated from *Acidovorax facilis* 72W genomic DNA. The newly defined ORF encodes an identifiable enzyme that converts nitrile to the corresponding carboxylic acid ammonium salt. The ORF was identified both on the basis of expression of active nitrilase as well as comparison of the nucleic acid and deduced amino acid sequences to public databases using algorithms well known in the art. The protein coded for by the ORF showed up to a 71% primary amino acid sequence identity to other known nitrilases.

Accordingly, preferred polypeptides of the instant invention are those active proteins that are at least 80% identical to the amino acid sequence reported herein. More preferred amino acid fragments are at least 90% identical to the sequences herein. Most preferred are amino acid fragments that are at least 95% identical to the amino acid fragments reported herein. Similarly, preferred nucleic acid sequences corresponding to the instant ORF are those encoding active proteins and which are at least 80% identical to the nucleic acid sequences reported herein. More preferred nucleic acid fragments are at least 90% identical to the sequences herein. Most preferred are nucleic acid fragments that are at least 95% identical to the nucleic acid fragments reported herein.

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

In general, a sequence of ten or more contiguous amino acids or thirty or more nucleotides is necessary to putatively identify a polypeptide or nucleic acid sequence as homologous to a known protein or gene. Moreover, with respect to nucleotide sequences, gene-specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers.

For example, genes encoding similar enzymes to that of the instant invention, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Sambrook, J., Fritsch, E. F. and Maniatis, T., Molecular Cloning: A Laboratory Manual (1989), Cold Spring Harbor Laboratory Press, Cold Spring Harbor (referred to throughout as "Maniatis"). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

Two short segments of the instant ORF may be used in polymerase chain reaction protocols to amplify longer nucleic acid fragments encoding homologous genes from DNA or RNA. Alternatively, the second primer sequence may be based upon sequences derived from the cloning vector. For example, the skilled artisan can follow the RACE protocol to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., PNAS USA (1989) 86:5673; Loh et al., Science (1989) 243:217).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the diagnosis of genetic disorders" (1986) pp. 33–50, in Human Genetic Diseases: A Practical Approach, K. E. Davis (Ed.), IRL Press, Herndon, Va.); Rychlik, W., PCR Protocols: Current Methods and Applications. (1993) 15:31–39, in Methods in Molecular Biology, B. A. White, (Ed.), Humania Press, Inc., Totowa, N.J.)

Alternatively, the instant sequences may be used as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected (cDNA, genomic DNA or RNA). The probe length can vary from 5 bases to tens of thousands of bases, the length depending upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined (Maniatis, particularly Chapter 11 and Table 11.1). Typically, the probe and sample must be mixed under conditions which will permit nucleic acid hybridization. This involves contacting the probe and sample in the presence of an inorganic or organic salt under appropriate temperature and ionic strength conditions. The probe and sample nucleic acids must be in contact for a long enough time that any possible hybridization between the probe and sample nucleic acid may occur. The concentration of probe or target in the mixture will determine the time necessary for hybridization to occur. The greater the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness et al., Nucl. Acids Res. (1991) 19:5143–5151). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be used. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kilodaltons), and serum albumin.

Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, *Adv. Immunol.* 36:1 (1984); and Maniatis).

Heterologous Host Cells:

The active *Acidovorax facilis* 72W nitrilase protein may be produced in heterologous host cells, preferably in microbial hosts. Particularly useful in the present invention will be cells that are readily adaptable to large-scale fermentation methods. Such organisms are well known in the art of industrial bioprocessing, examples of which may be found in "*Recombinant Microbes for Industrial and Agricultural Applications*", Murooka et al., eds., Marcel Dekker, Inc., New York, N.Y. (1994), and include fermentative bacteria as well as yeast and filamentous fungi. Host cells may include but are not limited to *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. Particularly preferred is *E. coli*. Examples of suitable *E. coli* host cells in which a nitrilase gene can be expressed include but are not limited to host cells specified herein and MG1655 (ATCC 47076), W3110 (ATCC 27325), MC4100 (ATCC 35695), W1485 (ATCC 12435), and their derivatives.

Microbial Expression Systems and Expression Vectors:

Microbial expression systems and expression vectors containing regulatory sequences that direct high level expression of foreign proteins are well known to those skilled in the art. These could be used to construct chimeric genes for production of the gene products of the 4.1 kb fragment of the invention. These chimeric genes could then be introduced into appropriate microorganisms via transformation to provide high level expression of the nitrilase enzymes. The nucleotides of the present invention may be used to produce gene products having enhanced or altered activity levels relative to that of the native gene sequence.

Additionally, chimeric genes will be effective in altering the properties of a host cell. For example, introducing at least one copy of chimeric genes encoding the present ORF under the control of the appropriate promoters into a host cell gives the host cell the ability to convert 2-methylglutaronitrile to 4-cyanopentanoic acid. The chimeric genes of the instant invention will comprise suitable regulatory sequences useful for driving gene expression of the present nitrilase sequences. Regulatory sequences will include, but are not limited to promoters, translation leader sequences, and ribosomal binding sites. It is preferred if these sequences are derived from the host organism; however, the skilled person will recognize that heterologous regulatory sequences may also be used.

In one embodiment, the regulatory sequences will include a promoter. Promoters may be constitutive or inducible. Inducible promoters are generally responsive to a specific stimulus (e.g., IPTG inducing the lac promoter). Inducible promoters may be responsive to a variety of stimuli, including, chemicals, growth cycle, changes in temperature, changes in pH and changes in osmolarity, to name only a few. In a preferred embodiment of the invention it has been discovered that a chimeric gene comprising a nitrilase coding regions (e.g., SEQ ID NO:4, SEQ ID NO:13 OR SEQ ID NO:15) is expressed as effectively, or more effectively in the absence of an inducer where the regulatory regions comprise an inducible promoter.

The chimeric gene is introduced into the appropriate host by cloning it into a suitable expression vector. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the DNA fragment which controls transcriptional termination. It is most preferred when both control regions are derived from genes homologous to the host cell, although such control regions need not be derived from the genes native to the specific species chosen as a production host.

Initiation control regions or promoters, which are useful to drive expression of the instant ORF in the desired host cell are numerous and familiar to those skilled in the art, including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $1P_L$, $1P_R$, T7, tac, $P_{BAD}$, and trc (useful for expression in *Escherichia coli*). Examples include at least one of the promoters selected from the groups consisting of the tryptophan operon promoter Ptrp of *E. coli*, a lactose operon promoter Plac of *E. coli*, a Ptac promoter of *E. coli*, a phage lambda right promoter PR, a phage lambda left promoter PL, a T7 promoter, and a promoter of the GAP gene from *Pichia pastoris*, or is at least one strong promoter selected from the group of microorganisms consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium,* and *Streptomyces*.

Termination control regions may also be derived from various genes native to the preferred hosts. Optionally, a termination site may be unnecessary; however, it is most preferred if included.

Additionally, the inserted genetic material may include a ribosome binding site. The ribosome binding site may be from a phage lambda CII gene or is selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

Optionally, the instant gene product may preferably be a secretion product of the transformed host. Secretion of desired proteins into the growth media simplifies purification procedures and reduces costs. Secretion signal sequences are often useful in facilitating the active transport of expressible proteins across cell membranes. A transformed host capable of secretion may be created by incorporating in the host a DNA sequence that codes for a secretion signal. Methods for choosing appropriate signal sequences are well known in the art (see for example EP 546049; WO 9324631). The secretion signal DNA may be located between the expression-controlling DNA and the instant coding sequence or coding sequence fragment, and in reading frame with the latter.

Fermentations, which may be run in the batch, fed-batch, or continuous mode, are common and well known in the art (Thomas D. Brock in *Biotechnology: A Textbook of Industrial Microbiology*, Second Edition (1989) Sinauer Associates, Inc.; Sunderland et al., *Appl. Biochem. Biotechnol.* (1992) 36:227.

The present nucleotide fragments may be used to produce gene products having enhanced or altered activity levels. Specifically, the nucleotide fragments can be used to produce a mutated microbial gene encoding a protein characterized by an increased nitrilase activity on nitrile-containing substrates and or an increased enzyme stability, one or both characteristics increased relative to the nitrilase activity of the native microbial gene. Various methods are known for mutating a native gene sequence to produce a gene product with altered or increased activity relative to the native gene sequence. These include, but are not limited to, directed evolution, random mutagenesis, domain swapping (using zinc finger domains, or restriction enzymes), rational design, error prone PCR (Melnikov et al., *Nucleic Acids Research* (1999) 27(4):1056–1062); site-directed mutagenesis (Coombs et al., in *Proteins* (1998) 259–311, R. H. Angeletti (Ed.), Academic Press, San Diego, Calif.), and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

Definitions of Abbreviations and Terms:

In this specification, a number of terms and abbreviations are used in the manner defined below.

The abbreviations in the specification correspond to units of measure, techniques, properties, or compounds as follows: "sec" means second(s), "min" means minute(s), "h" means hour(s), "d" means day(s), "μL" means microliter, "mL" means milliliters, "L" means liters, "mM" means millimolar, "M" means molar, "mmol" means millimole(s), "Ampr" means ampicillin resistance, "Amps" means ampicillin sensitivity, "kb" means kilo base, "kd" means kilodaltons, "nm" means nanometers, and "wt" means weight. "ORF" means open reading frame, "PCR" means polymerase chain reaction, "SSC" means saline-sodium citrate buffer, "HPLC" means high performance liquid chromatography, "ca" means approximately, "dcw" means dry cell weight, "O.D." means optical density at the designated wavelength, "IU" means International Units, "MGN" means 2-methylglutaronitrile, "4-CPA" means 4-cyanopentanoic acid, and "IPTG" means isopropyl β-D-thiogalactopyranoside.

"Enzyme catalyst" refers to a catalyst characterized by a specific nitrilase activity on nitrile-containing substrates.

"Hydrogenation catalyst" refers to a material that accelerates hydrogenation without itself being consumed or undergoing a chemical change. Hydrogenation catalysts suitable for use in this invention include, but are not limited to, the various platinum metals, such as iridium, osmium, rhodium, ruthenium, platinum, and palladium; also various other transition metals such as cobalt, copper, nickel and zinc. The catalyst may be unsupported, (for example, as Raney nickel or platinum oxide), or it may be supported (for example, as palladium on carbon, platinum on alumina, or nickel on kieselguhr).

The terms "host cell" and "host organism" refer to a cell capable of receiving foreign or heterologous genes, gene fragments, or DNA fragments.

The term "mesophilic baterium" refers to a bacterium living in the temperature range near that of warm-blooded animals, and usually showing a growth temperature optimum between 25 and 40° C.

The terms "recombinant organism", "transformed host", "transformant", "transgenic organism", and "transformed microbial host" refer to a host organism having been transformed with heterologous or foreign DNA. The recombinant organisms of the present invention express foreign coding sequences or genes which encode active nitrilase enzyme. "Transformation" refers to the transfer of a DNA fragment into the genome of a host organism, resulting in genetically stable inheritance. "Transformation cassette" refers to a specific fragment of DNA containing a set of genetic elements conveniently arranged for insertion into a host cell, usually as part of a plasmid. "Expression cassette" refers to a specific fragment of DNA containing a set of genetic elements conveniently arranged for insertion into a host cell, usually as part of a plasmid, that also allows for enhanced gene expression in the host.

The terms "plasmid" and "vector" refer to an extra chromosomal element often carrying genes which are not part of the central metabolism of the host cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction.

The term "nucleic acid" refers to complex compounds of high molecular weight occurring in living cells, the fundamental units of which are nucleotides linked together with phosphate bridges. Nucleic acids are subdivided into two types: ribonucleic acid (RNA) and deoxyribonucleic acid (DNA).

The letters "A", "G", "T", and "C" when referred to in the context of nucleic acids, mean the purine bases (Adenine ($C_5H_5N_5$) and Guanine ($C_5H_5N_5O$)) and the pyrimidine bases (Thymine ($C_5H_6N_2O_2$) and Cytosine ($C_4H_5N_3O$)), respectively.

The term "complementary" is used to describe the relationship between nucleotide bases that are hybridizable to one another. For example, with respect to DNA, adenosine is complementary to thymine and cytosine is complementary to guanine. cDNA is a single stranded DNA complementary to an RNA synthesized from it by reverse transcription in vitro. Anti-sense RNA is an RNA molecule complementary to another RNA.

The terms "coding sequence" or "coding region" refers to a DNA sequence that codes for a specific amino acid sequence. The terms "ORF" and "open reading frame" and "coding sequence" and "coding region" are used interchangeably to refer to a portion of DNA sequence that translates into a protein. ORFs are usually delineated in the sequence by three base pairs designating the start (a start codon) and three base pairs designating the stop (a stop codon) in the translation of the DNA sequence into the protein sequence.

The terms "nucleic acid fragment" or "nucleotide fragment" refer to a fragment of DNA that may encode a gene and/or regulatory sequences preceding (5', upstream) or following (3', downstream) the coding sequence. A "fragment" constitutes a fraction of the complete nucleic acid sequence of a particular region. A fragment may constitute an entire gene.

The terms "restriction endonuclease" and "restriction enzyme" refer to an enzyme which catalyzes hydrolytic cleavage within a specific nucleotide sequence in double-stranded DNA.

The term "oligonucleotide" refers to primers, probes, oligomer fragments to be detected, labeled-replication blocking probes, and oligomer controls, and refers generically to polydeoxyribonucleotides (containing 2-deoxy-D-ribose), to polyribonucleotides (containing D-ribose) and to any polynucleotide which is an N-glycoside of a purine or pyrimidine base (nucleotide), or modified purine or pyrimidine base. Also included in the definition of "oligonucleotide" are nucleic acid analogs (e.g., peptide nucleic acids) and those that have been structurally modified (e.g., phosphorothiolate linkages) (See also Thuong et al., *Biochimie* (1985) July–August 67(7–8):673–684.) There is no intended distinction between the length of a "nucleic acid", "polynucleotide" or an "oligonucleotide".

The term "primer" refers to an oligonucleotide (synthetic or occurring naturally), which acts as a point of initiation of nucleic acid synthesis or replication along a complementary strand when placed under conditions in which synthesis of a complementary strand is catalyzed by a polymerase.

The term "probe" refers to an oligonucleotide (synthetic or occurring naturally), that is significantly complementary to a "fragment" and forms a duplexed structure by hybridization with at least one strand of the fragment.

"Suitable regulatory sequences" refer to nucleotide sequences which influence the transcription, RNA processing, RNA stability, or translation of the associated coding sequence and which are located upstream (5' non-coding sequences), within, or downstream (3' noncoding sequences) of a coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Gene" refers to a nucleic acid fragment that expresses a specific protein, including regulatory sequences preceding (5' non-coding sequences) and following (3' non-coding sequences) the coding sequence. "Native gene" refers to a gene with its own regulatory sequences in an arrangement as found in nature. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of the native organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias.

The term "expression" means the transcription and translation to gene product from a gene coding for the sequence of the gene product, usually a protein.

The terms "protein", "polypeptide", and "peptide" are used interchangeably to refer to the gene product expressed.

"Mature" protein refers to a post-translationally processed polypeptide (i.e., one from which any pre- or pro-peptides present in the primary translation product have been removed). "Precursor" protein refers to the primary product of translation of mRNA (i.e., with pre- and pro-peptides still present). Pre- and pro-peptides may be, but are not limited to, intracellular localization signals.

The term "percent identity" is a relationship between two or more polypeptide sequences or two or more polynucleotide sequences, as determined by comparing the sequences. "Identity" also means the degree of sequence relatedness between polypeptide or polynucleotide sequences, as the case may be, as determined by the match between strings of such sequences.

"Similarity" is a descriptive term that only implies that two sequences, by some criterion, resemble each other and carries no suggestion as to their origins or ancestor. "Homology" refers specifically to similarity due to descent from a common ancestor. On the basis of similarity relationships among a group of sequences, it maybe possible to infer homology, but outside of an explicit laboratory model system, descent from a common ancestor remains hypothetical. (States et al., Similarity and Homogeneity (1992) pp. 89–92, in J. Sequence Analysis Primer, Gribskov, M. and Devereux, J., (Eds.), Freeman and Co.).

"Identity" and "similarity" can be readily calculated by known methods including, but not limited to, those described in *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, Totowa, N.J. (1994); *Sequence Analysis in Molecular Biology* (von Heinje, G., ed.) Academic Press (1987); and *Sequence Analysis Primer* (Gribskov, M. and Devereux, J., Eds.) Stockton Press, New York (1991). Preferred methods to determine identity are designed to give the best match between the sequences tested.

Preferred computer program methods to determine the identity and similarity between two sequences include, but are not limited to, the Wisconsin Package Version 9.0 and 10.0 Genetics Computer Group (GCG) Gap program found in the GCG program package, BLASTP, BLASTN, and FASTA (Pearson et al., *Proc. Natl. Acad. Sci. USA.* (1988) 85:2444–2448). The BLAST X program is publicly available from NCBI and other sources (BLAST Manual, Altschul et al., *Natl. Cent. Biotechnol. Inf.*, Natl. Library Med. (NCBI NLM) NIH, Bethesda, Md. 20894; Altschul et al., *J. Mol. Biol.* (1990) 215:403–410).

The term "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as substitution, deletion or insertion of one or more nucleotide bases that do not substantially affect the functional properties of the resulting transcript.

"Codon degeneracy" refers to the divergence in the genetic code permitting variation of the nucleotide sequence without affecting the amino acid sequence of an encoded polypeptide. For example, it is well known in the art that triplet codons CTT, CTC, CTA, and CTG all code for the amino acid leucine (Atlas, R., *Principles of Microbiology*). It is also well known in the art that alterations in a gene that produce a chemically-equivalent amino acid at a given site, but do not affect the functional properties of the encoded protein, are common. Thus, a codon for the amino acid alanine, a hydrophobic amino acid, may be substituted by a codon encoding another less hydrophobic residue (such as glycine) or a more hydrophobic residue (such as valine, leucine, or isoleucine) without affecting the functional properties of the encoded protein. Similarly, substitution of one negatively charged residue for another (such as aspartic acid for glutamic acid) or one positively charged residue for another (such as lysine for arginine) can also be expected to produce a functionally equivalent product. Nucleotide changes that result in alteration of the N-terminal and C-terminal portions of the protein molecule would also not be expected to alter the activity of the protein. Each of the proposed modifications is well within the routine skill in the art, as is determining if the biological activity of the encoded products is retained.

Moreover, the skilled artisan recognizes that substantially similar nucleotide sequences encompassed by this invention are also defined by their ability to hybridize, under stringent conditions, with the sequences exemplified herein. Typically, stringent conditions are those in which the salt concentration is less than about 1.5 M Na ion (typically about 0.01 to 1.0 M Na ion concentration or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved by adding destabilizing agents such as formamide. Exemplary low stringency conditions include hybridization with a buffer solution of 6×SSC (1 M NaCl), 30 to 35% formamide, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 6×SSC (1 M NaCl), 40 to 45% formamide, 1% SDS at 37° C., and a wash in 0.5× to 1×SSC at 55 to 60° C. Exemplary high stringency conditions include hybridization in 6×SSC (1 M NaCl), 50% formamide, 1% SDS at 37° C., and awash in 0.1×SSC at 60 to 65° C.

"Specificity" is typically a function of post-hybridization washes, the critical factors being the ionic strength and temperature of the final wash solution. The melting temperature $T_m$ of a probe-target hybrid can be calculated to provide a starting point for determining correct stringency conditions. The $T_m$ is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (*Anal. Biochem.* (1984) 138:267–284) as follows:

$$T_m = 81.5° \text{ C.} + 16.6(\log M) + 0.41(\% \ G+C) - 0.61(\% \text{ form}) - 500/L;$$

where M is the molarity of monovalent cations, % G+C is the percentage of guanosine and cytosine nucleotides in the DNA, % form is the percentage of formamide in the hybridization solution, and L is the length of the hybrid in base pairs.

$T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point $T_m$ for the specific sequence and its complement at a defined ionic strength and pH. However, severely stringent conditions can use a hybridization and/or wash at 1, 2, 3, or 4° C. lower than the thermal melting point $T_m$; moderately stringent conditions can use a hybridization and/or wash at 6, 7, 8, 9, or 10° C. lower than the thermal melting point $T_m$; and low stringency conditions can use a hybridization and/or wash at 11, 12, 13, 14, 15, or 20° C. lower than the thermal melting point $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe and G+C composition of the target DNA.

An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays" (1993) Elsevier, New York, and in *Current Protocols in Molecular Biology*, (1995) Chapter 2, Ausubel et al. (Eds.), Greene Publishing and Wiley-Interscience, New York.

General Methods

All HPLC methods were performed according to Gavagan et al., *J. Org. Chem.* (1998) 63:4792–4801.

For computational nucleic acid and protein sequence assembly and analyses (including determination of identity and similarity), Applicants used the Wisconsin Package Version 9.0 and 10.0 Genetics Computer Group (GCG) Gap program found in the GCG program package (using the Needleman and Wunsch algorithm with their standard default values of gap creation penalty=50 and gap extension penalty=3 (Devereux et al., *Nucleic Acids Res.* (1984) 12:387–395)), Sequencher Version and Vector NTI Deluxe v 4.0.3 software and database packages. Unless specified otherwise, all default parameters were used.

Materials and methods suitable for the maintenance and growth of bacterial cultures are well known in the art.

Techniques suitable for use in the following examples may be found as set out in Manual of Methods for General Bacteriology (1994) (Phillipp Gerhardt et al. (Eds.), American Society for Microbiology, Washington, D.C.) or as set out in Biotechnology: A Textbook of Industrial Microbiology (1989) Second Edition, (Thomas D. Brock, Sinauer Associates, Inc., Sunderland, Mass.).

Nitrile-containing substrates suitable for use in this invention are dinitriles having the formula NC—R—CN where R is an alkylene group having from about 1 to about 10 carbons. A more preferred nitrile-containing substrate is an aliphatic α,ω-dinitrile having the formula $NCCX_a(R)(CH_2)_nCN$, where a=0 or 1, where X=hydrogen when a=1, and R=H, alkyl or substituted alkyl, or alkenyl or substituted alkenyl, or alkylidene or substituted alkylidene, and where n=1 or 2. Most preferred for use as a nitrile-containing substrate in this invention is 2-methylglutaronitrile.

In an improved method for producing five-membered or six-membered ring lactams with biocatalysts comprising the biological units claimed herein, preferred is an aliphatic α,ω-dinitrile of either the formula:

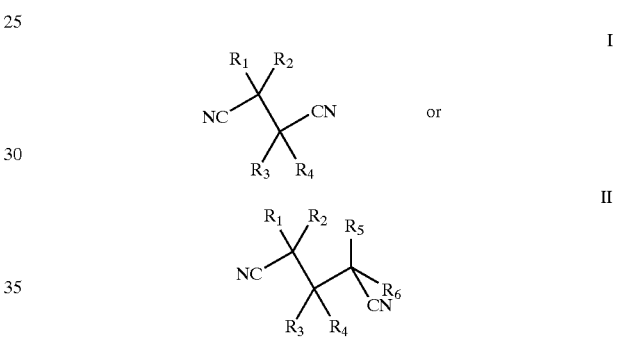

where $R_1$ and $R_2$ are both H, and $R_3$, $R_4$, $R_5$, and $R_6$ are each independently selected from the group consisting of H, alkyl or substituted alkyl, or alkenyl or substituted alkenyl, or $R_3$ and $R_4$ taken together are alkylidene or substituted alkylidene, or indepently $R_5$ and $R_6$ taken together are alkylidene or substituted alkylidene. A more preferred nitrile-containing substrate is an aliphatic α,ω-dinitrile unsymmetrically substituted at the α-carbon atom (See U.S. Pat. No. 5,858,736, incorporated herein by reference)

Procedures required for PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis; and by T. J. Silhavy et al. (in Experiments with Gene Fusions, (1984) Cold Spring Harbor Laboratory Press, Cold Spring, N.Y.); and by Ausubel et al. (in Current Protocols in Molecular Biology (1994–1998) John Wiley & Sons, Inc., New York).

A. Isolation and Partial Amino Acid Sequencing of the *Acidovorax facilis* 72W Nitrilase Enzyme:

The nitrilase of the present invention was isolated and refined to >90% purity from extracts of *Acidovorax facilis* 72W (ATCC 55746). Bacterial nitrilases are known to be generally comprised of one subunit (Novo et al., *FEBS Letters* (1995) 367:275–279). Methods to purify nitrilase enzymes are known in the art (Bhalla et al., *Appl. Microbiol. Biotechnol.* (1992) 37:184–190, Goldlust et al., *Biotechnol. Appl. Biochem.* (1989) 11:581–601, Yamamoto et al., *Agric.*

Biol. Chem. (1991) 55:1459–1466). The instant nitrilase was purified by passage through a Q-Sepharose ion exchange medium followed by gel filtration on a Hiload 16/60 Superdex 200 column. Methods to purify and separate enzymes are known in the art. (See, for example, Rudolph et al., Chromatogr. Sci. (1990) 51 (HPLC Biol. Macromol.):333–50.) Nitrilase activity was monitored during purification by measuring the rate of conversion of benzonitrile to benzoic acid as indicated by the increase in absorption at 245 nm of a 5 mM solution of benzonitrile in a 100 mM, pH 7.2 phosphate buffer.

N-terminal amino acid sequence and sequences of peptide digestion products from the purified Acidovorax facilis 72W nitrilase protein were determined. Nitrilase purified by gel filtration was sequenced following trypsin digestion using methods known to the art, including cysteine modification by reduction followed by alkylation with 4-vinylpyridine (See, for example, Matsudaira, Methods Enzymol. (1990) 182 (Guide Protein Purif.):602–13 or Allen, Sequencing of Proteins and Peptides. In: Laboratory Techniques in Biochemistry and Molecular Biology (Burdon, R. H. and van Knippenberg, P. H., Eds), Elsevier, Amsterdam, New York, Oxford (1989)).

Database searches were run on GCG using Wisconsin Software Package 9.1 (Genetics Computer Group, Madison, Wis.). Determined amino acid sequences were compared to protein sequence information contained in the SWISS-PROT database. Ten oligopeptides isolated from the digest of the purified Acidovorax facilis 72W nitrilase protein had amino acid sequences with >60% similarity to other known nitrilase proteins. This indicates that the purified protein has a high probability of containing a nitrilase enzyme.

B. Isolation of a DNA Fragment Containing the Nitrilase Gene and Expression in E. coli:

To identify possible DNA sequences with homology to known nitrilase genes, degenerate oligonucleotide primers were designed and synthesized for use as PCR primers. The design of these PCR primers was based on conserved coding regions found in bacterial nitrilase sequences available from the GenBank database (GenBank Accession Numbers D12583, J03196, D13419, L32589, D67026). Genomic DNA was isolated from Acidovorax facilis 72W (ATCC 55746) by standard methods (Maniatis) modified by adding two rounds of phenol-chloroform extraction. DNA so isolated was used as a target for PCR with numerous degenerate primer combinations. The resulting amplified products were cloned into the pGem-T vector and sequenced by methods common to the art. From experiments with ten different PCR primer pairs, only one product found in plasmid pJJ 28–5, resulting from primers 1F (SEQ ID NO:1) and 7R (SEQ ID NO:2), yielded a 385 bp DNA fragment (SEQ ID NO:3) with 74.1% identity to a region of the nitrilase DNA sequence from Rhodococcus rhodochrous K22 (GenBank Accession Number D12583). In addition, the putative protein product from this 385 bp DNA fragment contained a number of peptide sequences matching those isolated from the purified 72W nitrilase protein digest. This was additional evidence that the identified 385 bp fragment contained a portion of the desired 72W nitrilase gene.

With the discovery of this partial gene sequence with high homology to other known nitrilase genes, Applicants have discovered a piece of DNA useful as a probe to identify recombinant clones containing the 72W nitrilase gene in any DNA library. In addition, the successful use of SEQ ID NO:1 and SEQ ID NO:2 as degenerate PCR primers to discover a novel nitrilase gene shows that Applicants have discovered DNA sequences that have general utility as a means of identifying and isolating unknown nitrilases from bacterial strains.

In order to map the complete nitrilase gene to a single restriction fragment, Southern hybridizations were performed on Acidovorax facilis 72W genomic DNA. High molecular weight genomic DNA was isolated from Acidovorax facilis 72W cells by using Qiagen genomic tip-100/G DNA isolation kit (Qiagen Inc., USA). 1 μg genomic DNA was digested with a variety of restriction enzymes, resolved on 1% agarose gel followed by transfer to nylon membrane. Restriction fragments immobilized on nylon membrane were probed with 385 bp partial nitrilase fragment (SEQ ID NO:3) by Southern hybridizations. The nitrilase gene was mapped to a single restriction fragment when genomic DNA was digested with any of the following restriction enzymes: BamHI, BclI, BglII, ClaI, EagI, KpnI, NarI, NheI, NotI, NsiI, PstI, SalI, SpeI, SstI, XbaI, XhoI. These observations provided strong evidence for the presence of a single nitrilase gene in Acidovorax facilis 72W (ATCC 55746). EcoRI digests, from the known partial gene sequence (SEQ ID NO:3) which contains an EcoRI site within itself, yielded two bands. Digests with PstI yielded a single, 4.1 kb band that reacted with the probe, suggesting that the nitrilase homolog was present on a 4.1 kb PstI fragment from the chromosome. This information was critical for selecting a restriction enzyme (in this case PstI) to generate an enriched library of genomic fragments to isolate the complete nitrilase gene.

To construct a library, Acidovorax facilis 72W genomic DNA was digested with PstI and resolved by gel electrophoresis. Fragments ranging in size from 2.5–7 kilobases were recovered from the gel and ligated into the vector pBluescript II SK(+) (Stratagene, La Jolla, Calif., USA). The ligated DNA was electrotransformed into E. coli DH10B electromax cells (Life Technologies, Rockville, Md., USA). The resultant library represented $4 \times 10^6$ independent, recombinant clones of Acidovorax facilis 72W PstI fragments. In order to screen the library, plasmids were prepared from cells scraped from plates.

The above plasmid library was transformed into E. coli DH5α. A labeled probe fragment containing the 385 bp nitrilase gene fragment from pJJ28-5 was used to screen the library by colony hybridization. Three colonies that showed positive hybridization with the nitrilase probe were grown in liquid cultures in the presence of ampicillin. Plasmids from these colonies (pnit4, pnit5, and pnit6) showed identical restriction fragment patterns when digested with PstI, EcoRI, and HindIII, suggesting that these plasmids contained identical inserts. PstI digestion yielded a 4.1 kb insert fragment confirming Southern hybridization results. Inserts in all the above plasmids contained one internal EcoRI and one HindIII site, respectively, as expected from the partial gene sequence already identified (SEQ ID NO:3).

The inserts in plasmids pnit4, pnit5, and pnit6 had identical nucleotide sequences (SEQ ID NO:4) containing an ORF encoding a 369 amino acid sequence (SEQ ID NO:5) similar in length to other nitrilases. The primary amino acid sequence is 71% identical to the nitrilase from Rhodococcus rhodochrous K22 (GenBank Accession Number D12583). The ORF start codon is GTG, which yields a protein beginning with a valine instead of a more common start of methionine. The amino acid sequence (SEQ ID NO:5) encoded by the above ORF (SEQ ID NO:4) was scanned in the PROSITE database of protein families and domains using Scanprosite (www.Espay.ch/tools/scnpsitl.html) and Profilescan (www.isrec.isb-sib.ch/software/PFSCAN-form.html) and was found to contain signature patterns conserved in all known nitrilases. Based on this data, cysteine at position 164 (SEQ ID NOs:5 and 14) is proposed to be the active site cysteine in *Acidovorax facilis* 72W nitrilase. The sequence similarity to known nitrilases as well as the presence of the nitrilase signature together provided evidence that the gene for nitrilase was present on the 4.1 kb PstI fragment of pnit4, pnit5, and pnit6 on an ORF (SEQ ID NO:4) encoding a 369 amino acids sequence (SEQ ID NO:5).

The instant invention thus provides a plasmid clone DH5α:pnit4 containing the complete *Acidovorax facilis* 72W nitrilase gene and the flanking chromosomal DNA in a form convenient for manipulation.

The *Acidovorax facilis* 72W nitrilase ORF identified in the 4.1 kb PstI fragment from pnit4 was cloned into a number of pet expression vectors based on T7 promoter-T7 RNA polymerase system for overexpression (Studier et al., *Meth. Enzymol.* (1990) 185:60–89). More specifically, the ORF was cloned into pET-3c and pET-21a (both, Novagen, Madison, Wis.). The pET-3c nitrilase construct (pnitex2 (Example 6)) and pET-21a construct (pSW91(Example 7)) both have the start codon (GTG) of native nitrilase ORF replaced with ATG. An additional pET-21a construct (pSW90 (Example 7)) yields a modified form that contains an 11 amino acid T7 tag fusion at the N-terminus of the protein. The plasmid pnitex2 was transformed into two different host strains BL21(DE3) and BL21-SI yielding strains SS1001 and SS1002 respectively (Example 6). These strains allowed expression of nitrilase with or without induction by IPTG (strain SS1001, Example 6) or induction by NaCl (strain SS1002, Example 6). The plasmids pSW90 and pSW91 were transformed into BL21(DE3) yielding strains SW90 and SW91 respectively (Example 7) both of which expressed enzymatically active nitrilase with or without induction by IPTG. When the above *E. coli* strains containing these constructs were induced according to protocols provided by the manufacturer, SS1001, SW90, and SW91 produced a specific protein of the expected molecular weight, approximately 40 kd. In addition, when tested for nitrilase enzyme activity (indicated by the ability to catalyze the conversion of MGN to 4-CPA), all expression systems (SS1001, SS1002, SW90, and SW91) catalyzed this reaction, showing that the genetically engineered *E. coli* strains were able to produce active *Acidovorax facilis* 72W nitrilase enzyme (Examples 6 and 7).

C. Production of *Acidovorax facilis* 72W (ATCC 55746) and *E. coli* Expression Strains Growth of *Acidovorax facilis* Strain 72W (ATCC 55746)

One frozen seed lot vial was thawed and the 1 mL contents placed in 500 mL of sterile Inoculum Medium listed below. The inoculum was grown at 30° C. with shaking at 250 rpm in a 2 L flask for 24–30 h.

| Inoculum Medium | |
|---|---|
| Component: | Final Concentration: |
| Potassium phosphate, monobasic | 1.5 g/L |
| Potassium phosphate, dibasic | 3.4 g/L |
| Ammonium sulfate | 1.5 g/L |
| Trisodium citrate, dihydrate | 1 g/L |
| Magnesium sulfate, heptahydrate | 0.4 g/L |
| Trace metal solution (below) | 1 mL/L |
| Amberex 695 (Universal Foods) | 1 g/L |
| Glycerol (sterilized separately) | 8 g/L |

| Trace Metal Solution | |
|---|---|
| Component: | Stock Concentration: |
| Hydrochloric Acid | 10 mL/L |
| Calcium chloride, dihydrate | 11.4 g/L |
| Manganese Sulfate, monohydrate | 1.23 g/L |
| Copper sulfate, pentahydrate | 0.63 g/L |
| Cobalt chloride, hexahydrate | 0.16 g/L |
| Boric Acid | 0.91 g/L |
| Zinc sulfate, heptahydrate | 1.77 g/L |
| Sodium molybdate, dihydrate | 0.05 g/L |
| Vanadyl sulfate, dihydrate | 0.08 g/L |
| Nickel nitrate, hexahydrate | 0.04 g/L |
| Sodium selenite | 0.04 g/L |
| Ferrous sulfate, heptahydrate | 6.0 g/L |

The inoculum from the shake flask was transferred aseptically to a presterilized Braun Biostat C fermenter containing the Fermenter Medium listed below.

| Fermenter Medium | |
|---|---|
| Component: | Final Concentration: |
| Potassium phosphate, monobasic | 0.39 g/L |
| Potassium phosphate, dibasic | 0.39 g/L |
| Difco yeast extract | 5.0 g/L |

Growth occurred under the following conditions: 32° C., pH 6.8–7.0, dissolved oxygen at 25% of saturation. At inoculation, the fermenter contained 8.5 L of Fermenter Medium plus 218 g of Nutrient Feed solution, giving a starting concentration of approximately 7 g/L glycerol. The Nutrient Feed solution included the following components which were sterilized separately and combined after cooling: potassium phosphate, monobasic, 19.6 g in 0.25 L deionized water; magnesium sulfate, heptahydrate, 3.3 g, plus sulfuric acid, 4 mL, in 0.15 L deionized water; Trace Metal solution, 67 mL, plus 400 g glycerol in 0.80 L deionized water. At 18 h post inoculation, feeding of Nutrient Feed solution began. Initially, the Nutrient Feed solution was added at a rate of 0.4 g feed/minute (0.15 g glycerol/min). The culture optical density measured at 550 nm (O.D. 550) was approximately 8–9. At 26 h, the O.D. 550 was 16–18 and the feed rate was increased to 0.9 g feed/min (0.3 g glycerol/min). A final increase in feed rate to 1.8 g feed/min (0.6 g glycerol/min) was made at 34 h. This rate continued to the end of the run (about 42 h). The final O.D. 550 was approximately 65–75 and equivalent to a cell density of 25–30 g dcw/L.

Cells were recovered by centrifugation and stored frozen until use. For use as a biocatalyst, cells were heated to 50° C. for 1 h in 0.35 M phosphate buffer (pH 7.3) and then used to catalyze the transformation of MGN into 4-CPA.

Growth of *E. coli* Cells for Whole Cell Activity and Immobilization:

25 mL of overnight culture of *E. coli* strain SS1100 grown from a single colony was inoculated into 250 mL fresh LB medium. The cultures were grown to mid-log phase and harvested by centrifugation with or without induction with 1 mM IPTG for 1 h. The strain SS1002 was grown in LBON (LB without NaCl) medium and induced with 0.2 M NaCl for 1 h at mid-log phase according to manufacturer's instructions for BL21-SI overexpression strain (Life Technologies, Rockville, Md., USA). The bacterial cell pellets were stored on ice overnight prior to measurement of nitrilase activity. For immobilization, E. coli strain SS1001 was grown in a 10 L batch fermentation in LB medium to an O.D. at 600 nm of 8.6. Cells were harvested by centrifugation and stored on wet ice for whole cell activities and immobilization.

Comparing the weight-specific activity of biocatalyst produced from the native strain, as described above, to the genetically engineered biocatalysts from Examples 6, 7, and 15 it is clear that the expression strains SS1001, SS1011, and SW91 produced biocatalysts of substantially greater specific activity (Table 2 in Example 6, Tables 3 and 4 in Example 7, and Table 5 in Example 15) than that of the native strain (Tables 2, 3, 4, and 5).

EXAMPLE 1

Purification of Nitrilase Protein

All steps in this procedure were performed at 5° C. and at pH 7.5 unless otherwise stated.

A 25 wt % suspension of *Acidovorax facilis* 72W (ATCC 55746) wet cell paste was prepared in 20 mM Tris, pH 7.5, 0.1 mM phenyl methyl sulfonyl fluoride (PMSF), and 2.0 mM dithiothreitol.

An extract of this suspension was prepared by passage through a French press (American Instrument Co., Silver Springs, Md., USA) according to methods known to the art. Following a centrifugation at 27,500 g for 30 min to remove cell debris, a 20–55% ammonium sulfate fractionation of the extract was prepared and then concentrated by overnight precipitation following the addition of solid ammonium sulfate to 65% of saturation. The concentrated protein precipitate was reconstituted using a minimum volume of 20 mM Tris, pH 7.5 (Buffer A) and desalted over a PD10 column containing Sephadex G-25 resin (Pharmacia).

Following desalting, the concentrated protein extract was fractionated by anion exchange chromatography using a column containing 50 mL of Q-Sepharose fast flow (Pharmacia). After loading the column with the concentrated protein extract, the column was washed with three column volumes of Buffer A at a flow rate of 2 mL/min to remove un-adsorbed protein. Adsorbed protein was eluted from the column using a 0–0.5 M NaCl gradient prepared in Buffer A. Elution of protein from the column was monitored at 280 nm. Nitrilase activity was monitored throughout purification using an assay measuring the hydrolysis of benzonitrile to produce benzoic acid. Nitrilase activity eluted at 0.4 M NaCl. Protein components in the 0.4 M NaCl protein fraction were separated by gel electrophoresis (SDS-PAGE) performed under reducing conditions (5% β-mercaptoethanol) on a 10–15% SDS polyacrylamide gel. Greater than 50% of the 0.4 M NaCl protein fraction consisted of a protein with subunit molecular weight of 39.7 kd. This is within the expected molecular weight range for nitrilase enzymes (Cowan et al., *Extremophiles* (1998) 2:207–216). Using methods known to the art, the native molecular weight of the nitrilase was determined to be 570 kd following gel filtration chromatography in 20 mM phosphate buffer at pH 7 using a Hiload 16/60 Superdex 200 column (Pharmacia) which had been calibrated using gel filtration MW standards (Pharmacia #17-0442-01). Following gel filtration, the nitrilase protein was >90% pure. The specific activity of the purified enzyme was determined to be 35 IU/mg protein using 2-methylglutaronitrile as substrate at 25° C.

EXAMPLE 2

Isolation of a DNA Fragment Showing High Homology to Known Nitrilases

Genomic DNA was isolated from *Acidovorax facilis* 72W (ATCC 55746) by standard methods (Maniatis) modified by adding two rounds of phenol-chloroform extraction. DNA so isolated was used as a target for amplification by PCR using primers 1F (SEQ ID NO:1) and 7R (SEQ ID NO:2). The resulting amplified products were cloned into the pGem-T vector (Promega, Madison, Wis.) and sequenced by methods common to the art. Clone pJJ 28-5 yielded a 385 bp DNA fragment (SEQ ID NO:3) with 74.1% identity to a region of the nitrilase DNA sequence from *Rhodococcus rhodochrous* K 22 (GenBank Accession Number D12583).

EXAMPLE 3

Localization of a Chromosomal Fragment Containing a Sequence with High Homology to the 385 bp Partial-Gene Fragment 1–3 µg high molecular weight genomic DNA samples from *Acidovorax facilis* 72W were digested with restriction enzyme PstI in a buffer supplied by the manufacturer (Life Technologies (Gibco-BRL), Gaithersburg, Md., USA). Digested samples were resolved on agarose gels and Southern-blotted on nylon membrane. Cutting at restriction sites flanking the insert, a probe containing the 385 bp nitrilase gene fragment (SEQ ID NO:3) was prepared from pJJ28-5. Hybridizations were carried out at 60° C. followed by high stringency washes (0.1×SSC, 0.1% SDS, 60° C. for 15 min). Probe labeling, hybridization and detection for dot blots and subsequent Southern blotting experiments, were performed using ECL random prime labeling and detection systems version II, (Amersham International plc, Buckinghamshire, England).

Digests with PstI yielded a single 4.1 kb band upon hybridization with the probe indicating that the nitrilase gene was present on a 4.1 kb PstI fragment of the *Acidovorax facilis* 72W genome.

EXAMPLE 4

Construction of *Acidovorax facilis* 72W (ATCC 55746) Genomic Library

5 µg high molecular weight genomic DNA from *Acidovorax facilis* 72W was digested with PstI and resolved on a preparative 1% agarose gel. Fragments ranging in size from 2.5 to 7 kb were recovered from the gel and ligated into PstI digested and dephosphorylated pBluescript II SK(+) vector (Stratagene, La Jolla, Calif., USA). The ligated DNA was electrotransformed into *E. coli* DH10B electromax cells (Life Technologies (Gibco-BRL), Gaithersburg, Md., USA) and transformed cells were plated on LB+ ampicillin (100 µg/mL)+IPTG+X-Gal plates. The resultant library with 95% recombinant plasmids represented 4×10⁶ independent recombinant clones. For library screening and storage, plasmids were prepared from the cells scraped from the plates.

The above plasmid library was transformed into *E. Coli DH5α* (Life Technologies, Rockville, Md., USA) cells and the transformants were plated on LB+ampicillin 100 µg/mL plates. After incubating overnight at 37° C., well-isolated colonies were transferred to nylon membrane and lysed in situ to immobilize DNA on membrane. The membranes were probed with labeled nitrilase gene probe described in Example 3. Three colonies that showed positive hybridization with the nitrilase probe were grown in liquid cultures in the presence of ampicillin. Plasmids pnit4, pnit5, and pnit6 yielded identical patterns upon digestion with restriction enzymes PstI, EcoRI, and HindIII respectively. These results confirmed that identical inserts were present in pnit4, pnit5, and pnit6. Restriction digests yielded a 4.1 kb PstI insert as expected from earlier Southern hybridization.

EXAMPLE 5

Sequence of *Acidovorax facilis* 72W (ATCC 55746) Nitrilase ORF

The 4.1 kb insert in plasmid pnit4 was sequenced using the standard Sanger dideoxy chain termination method. Sequence analyses using GCG MAP and Vector NTI software revealed the presence of an 1110 bp open reading frame (SEQ ID NO:4; SEQ ID NO:15, bases 332–1441). This ORF was present within a BclI-BglII fragment (SEQ ID NO:15, and FIG. 1) of the pnit4 insert. A search of GenBank sequence database revealed that this open reading frame (SEQ ID NO:4) had 68% identity to the nitrilase ORF from *Rhodococcus rhodochrous* K22 (GenBank Accession Number D12583). The 369 amino acids sequence (SEQ ID NO:5) deduced from the open reading frame (SEQ ID NO:4) is 71% identical to the *Rhodococcus rhodochrous* K22 nitrilase protein. A scan of the amino acid sequence (SEQ ID NO:5) encoded by *Acidovorax facilis* 72W ORF (SEQ ID NO:4) into the PROSITE database of protein families and domains using Profilescan and Scanprosite tools revealed the presence of signature patterns conserved for all known nitrilases.

EXAMPLE 6

Expression of *Acidovorax facilis* 72W (ATCC 55746) Nitrilase in *E. coli*

Oligonucleotides SEQ ID NO:6 and SEQ ID NO:7 were used in a PCR reaction to amplify the nitrilase ORF from *Acidovorax facilis* 72W (ATCC 55746) genomic DNA. The PCR product was digested with NdeI and BamHI and was cloned into NdeI-BamHI linearized pET-3c. The start codon of nitrilase ORF in the resultant expression plasmid (pnitex2) is ATG (SEQ ID NO:13) instead of the native GTG codon (SEQ ID NO:4). Accordingly, the amino acid sequence of the nitrilase expressed from pnitex2 has M (methionine) at position 1 (SEQ ID NO:14) instead of the native V (valine) of *Acidovorax facilis* 72W nitrilase (SEQ ID NO:5). Plasmids pnitex2 and pET-3c (control) were transformed into *E. coli* strains BL21(DE3) (Novagen, Madison, Wis., USA) to yield SS1001 and BL21(DE3): pET-3c, respectively.

Strains resulting from transforming pnitex2 and pET-3c into BL21-SI (Life Technologies, Rockville, Md.) were named SS1002 and BL21-SI:pET-3c, respectively. Plasmid pnitex2 contains nitrilase coding sequence under the control of T7 promoter. Transcription of chromosomally located T7 RNA polymerase, which regulates transcription of a gene under control of the T7 promoter (in this case the chimeric nitrilase gene), is induced by the addition of IPTG in host strain BL21 (DE3) and by the addition of NaCl in host BL21-SI. The above *E. coli* transformants, SS1001 (and the control strain BL21(DE3): pET-3c) and SS1002 (and the control strain BL21-SI: pET-3c), were grown in shake flasks or 10 L fermenters and chimeric nitrilase gene expression was measured with or without induction by adding either IPTG or NaCl following protocols provided by the manufacturers. Crude extracts of strains SS1001, SS1002, and BL21(DE3): pET-3c were prepared and run on SDS-PAGE gels with 5–20 μg total protein per lane. Molecular weight and laser densitometer analysis of the SDS-PAGE gel determined that the strains SS1001 and SS1002 expressed a specific protein band of approximately 40 kd size, corresponding to the expected size of *Acidovorax facilis* 72W nitrilase protein. This band represented >50% of total soluble protein in SS1001. The corresponding band was absent in the BL21(DE3): pET-3c crude extracts. Enzyme assays of the extracts from SS1001 suggested that 12% of total soluble protein was enzymatically-active nitrilase.

Whole cells of *E. coli* transformants SS1001 and SS1002, along with control strains BL21(DE3): pET-3c and BL21-SI: pET-3c, respectively, were also tested for nitrilase activity. The above transformants were grown to late log phase and the nitrilase activity levels of whole cells with or without induction was compared to the activity of strains harboring the control pET-3c vector only (Table 2). The nitrilase activity was measured by determining the rate of 4-CPA production from MGN. A 50 mg (dry cell weight)/mL cell suspension was prepared in 0.10 M potassium phosphate buffer, pH 7.0. Into a 20-mL glass scintillation vial equipped with a magnetic stir bar was added 3.0 mL of an aqueous solution of 0.40 M MGN at 25° C. With stirring, 1.0 mL of the cell suspension at 25° C. was added. At 5, 10, and 15 minutes after the addition of the cell suspension, a 180 μL aliquot was removed from the reaction mixture, mixed with 5 μL of 6.0 N HCl and 20 μL of 0.75 M N-methylpropionamide in water (HPLC external standard), centrifuged, and the supernatant analyzed by HPLC for the rate of production of 4-CPA ammonium salt.

A unit of nitrilase activity (IU) is equivalent to production of 1 micromole 4-CPA ammonium salt/min. The activity level is reported as units per gram of dry cell weight and compared to the activity of *A. facilis* 72W.

TABLE 2

Nitrilase Activity in *E. coli* transformants

| Transformant Catalyst | Induction | Nitrilase Activity (IU/g dry cell weight) |
|---|---|---|
| *E. coli* SS1001 (BL21(DE3):pnitex2) | None | 360 |
| *E. coli* SS1001 (BL21(DE3):pnitex2) | IPTG | 466 |
| *E. coli* control (BL21 (DE3):pET-3c) | IPTG | 0 |
| *E. coli* SS1002 (BL21-SI: pnitex2) | NaCl | 288 |
| *E. coli* control (BL21-SI: pET-3c) | None | 0 |
| *Acidovorax facilis* 72W (ATCC 55746) | Not applicable | 271 |

EXAMPLE 7

Expression of *Acidovorax facilis* 72W Nitrilase Gene in *E. coli*

The 72W nitrilase coding sequence was isolated from *Acidovorax facilis* 72W by PCR using primers corresponding to DNA sequence determined at the 5' and 3' ends of the coding sequence. The coding sequence was amplified using primers identified as SEQ ID NO:8 and SEQ ID NO:9 and subcloned into pGEM-T (Promega, Madison, Wis.). The primer identified as SEQ ID NO:8 changes the native GTG start codon to ATG. The nitrilase gene fragment was then removed from pGEM-T with BamHI and SacI and subcloned into the *E. coli* expression vector pET-21a (Novagen, Madison, Wis.), between BamHI and SacI to generate plasmid pSW90, such that an 11 amino acid T7 tag was encoded at the N-terminus of the nitrilase coding sequence. The coding sequence was also amplified using primers identified as SEQ ID NO:10 and SEQ ID NO:9 and subcloned into pGEM-T. The primer identified as SEQ ID NO:10 changes the native GTG start codon to ATG. The gene fragment was then removed from pGEM-T with NdeI and subcloned into pET-21a at the NdeI site to generate plasmid pSW91, such that no modifications (except for the start codon as described) were made to the native nitrilase coding sequence. Plasmids pSW90 and pSW91 were transformed into *E. coli* strain BL21(DE3) (Novagen, Madison, Wis.), to generate strains SW90 and SW91, respectively. After standard growth and induction (Novagen recommendations) of SW90 and SW91, cell extracts were prepared and examined by SDS-PAGE, and a major protein band of the expected size, ~40 kDa, corresponding to 72W nitrilase protein, was observed. In the case of SW91, the nitrilase protein on the PAGE gel represented >50% of total soluble protein. No comparable major band was observed in the control.

*E. coli* transformant SW91 expressing the *Acidovorax facilis* 72W (ATCC 55746) nitrilase coding sequence was tested for nitrilase activity by measuring the rate of 4-CPA production from MGN as described in Example 6.

Following growth and EPTG induction as recommended by the manufacturer (Novagen, Madison Wis.), the nitrilase activity level of SW91 was measured and compared to the activity of a control transformant harboring the expression vector without the nitrilase gene, and to typical activity observed for *A. facilis* 72W. The results are shown in Table 3. One unit of nitrilase activity (IU) is equivalent to production of 1 micromole 4-CPA ammonium salt/min, and is reported as units per gram of dry cell weight.

TABLE 3

Nitrilase activity in SW91 after standard growth and induction

| Strain | Nitrilase Activity (IU/g dry cell weight) |
|---|---|
| *E. coli* SW91 (BL21(DE3):pSW91) | 551 |
| *E. coli* control (BL21(DE3:pET-21a) | 0 |
| *Acidovorax facilis* 72W (ATCC 55746) | 271 |

*E. coli* transformant SW91 was also grown at 37° C. with shaking in LB media (Maniatis) without IPTG induction until saturation (12–16 h), after which cells were harvested by centrifugation and assayed for nitrilase activity. The results are shown in Table 4, and compared to typical activity observed for *A. facilis* 72W.

TABLE 4

Nitrilase activity in SW91 after growth to saturation without induction

| Strain | Nitrilase Activity (IU/g dry cell weight) |
|---|---|
| *E. coli* SW91 (BL21(DE3):pSW91) | 662 |
| *Acidovorax facilis* 72W (ATCC 55746) | 271 |

EXAMPLE 8

Immobilization of *Acidovorax facilis* 72W or *E. coli* Transformant SS1001 Cells in Carrageenan Into a 250 mL media bottle (equipped with magnetic stir bar and containing 64.12 g of distilled, deionized water at 50° C.) was slowly added 3.38 g of FMC BioPolymer ISAGEL® RG300 carrageenan with rapid stirring. The mixture was heated to 75–80° C. with rapid stirring until the carrageenan was completely dissolved, and the resulting solution cooled to 55–56° C. (gelling temperature ca. 52° C.) in a thermostated water bath. A suspension of either *Acidovorax facilis* 72W cells or *E. coli* transformant SS1001 (12.5% dry cell weight) in 0.35 M sodium hydrogen phosphate buffer (45 mL total volume, pH 7.3) was heated to 50° C. for 60 min (*Acidovorax facilis* 72W) or 12 min (*E. coli* transformant SS1001), then added to the carrageenan solution at 55–56° C. with stirring. The cell/carrageenan mixture was immediately added slowly to 450 mL of soybean oil at 50° C. with stirring using an overhead stirrer. After cell/carrageenan droplets of the desired size were produced in the oil by controlling the stirring rate, the temperature of the oil was reduced to 35° C. to gel the droplets, and the oil decanted from the resulting beads, which were washed with 0.10 M potassium bicarbonate buffer (pH 7.3). A 20-gram portion of the beads were resuspended in 48.8 mL of 0.10 M potassium bicarbonate buffer (pH 7.3), 0.25 g of 25 wt % glutaraldehyde in water was added, and the beads mixed for 1.0 h at 25° C. To the mixture was then added 1.0 g of 12.5 wt % polyethylenimine (BASF Lupasol® $PR_{971}L$, average Mw ca. 750,000) in water and the beads mixed for an additional hour at 25° C. The crosslinked beads were then washed with 50 mL of 0.30 M ammonium bicarbonate (pH 7.3) at 25° C. and stored in this same buffer at 5° C.

EXAMPLE 9

Comparison of Carrageenan-Immobilized *Acidovorax facilis* 72W and *E. coli* Transformant SS1001 Cells as Catalyst for Production of 4-Cyanopentanoic Acid Ammonium Salt In a typical reaction, 16.5 g of immobilized cell/carrageenan beads were placed into a 125 mL jacketed reaction vessel that was temperature-controlled at 30° C. with a recirculating temperature bath. To the reaction vessel was added 69.25 mL of water and 14.25 mL (13.54 g, 1.25 M) of 2-methyglutaronitrile, and the mixture stirred at 30° C. Samples (0.100 mL) were mixed with 0.400 mL of water, then 0.360 mL of the diluted sample was mixed with 0.040 mL of 0.75 M N-methylpropionamide in water and 0.020 mL of 6.0 N HCl. The resulting mixture was filtered (0.22 µm) and the filtrate analyzed by HPLC for 2-methylgluratonitrile, 4-cyanopentanoic acid and 2-methlglutaric acid. The rates of production of 4-cyanopentanoic acid when using carrageenan-immobilized *Acidovorax facilis* 72W and *E. coli* transformant SS1001 cells were 184 mM/h and 310 mM/h, respectively. At complete conversion of 2-methylglutaronitrile, each catalyst produced 4-cyanopentanoic acid ammonium salt and 2-methylglutaric acid diammonium salt in 98.7% and 1.3% yields, respectively.

EXAMPLE 10

Immobilization of *E. coli* Transformant SW91 Cells in Calcium Alginate

Into a 100 mL media bottle (equipped with magnetic stir bar and containing 22.9 g of distilled, deionized water at 50° C.) was slowly added 1.10 g of FMC BioPolymer Protanal® LF 10/60 alginate with rapid stirring. The mixture was heated to 75–80° C. with rapid stirring until the alginate was completely dissolved, and the resulting solution cooled to 25° C. in a water bath. A suspension of *E. coli* transformant SW91 (50% wet cell weight, 11.5% dry cell weight) in 0.15

M sodium acetate buffer (16 mL total volume, pH 7.0) was added to the alginate solution at 25° C. with stirring. The cell/alginate mixture was added dropwise by syringe to 213 mL of 0.20 M calcium acetate buffer (pH 7.0) at 25° C. with stirring. After stirring for 2 h, the buffer was decanted from the resulting beads, which were resuspended in 84 mL of 0.20 M calcium acetate buffer (pH 7.0) at 25° C. With stirring, 0.88 g of 25 wt % glutaraldehyde in water was added and the beads mixed for 1.0 h at 25° C. To the mixture was then added 3.5 g of 12.5 wt % polyethylenimine (BASF Lupasol® PR971L, average Mw ca. 750,000) in water and the beads mixed for an additional 1 h at 25° C. The crosslinked beads were then washed twice with 84 mL of 0.20 M calcium acetate buffer (pH 7.0) at 25° C. and stored in this same buffer at 5° C.

EXAMPLE 11

Calcium Alginate-Immobilized *E. coli* Transformant SW91 Cells as Catalyst for Production of 4-Cyanopentanoic Acid Ammonium Salt Into a 125 mL jacketed reaction vessel (temperature-controlled at 30° C. with a recirculating temperature bath) was placed 16.5 g of *E. coli* SW91/alginate beads prepared as described in Example 10. To the reaction vessel was added 68.25 mL of water, 1.0 mL of 0.20 M calcium acetate buffer (pH 7.0), and 14.25 mL (13.54 g, 1.25 M) of 2-methyglutaronitrile, and the mixture stirred at 30° C. Samples (0.100 mL) were mixed with 0.400 mL of water, then 0.360 mL of the diluted sample was mixed with 0.040 mL of 0.75 M N-methylpropionamide in water and 0.020 mL of 6.0 N HCl. The resulting mixture was filtered (0.22 µm) and the filtrate analyzed by HPLC for 2-methyglutaronitrile, 4-cyanopentanoic acid and 2-methlglutaric acid. The rate of production of 4-cyanopentanoic acid was 739 mM/h, and the reaction was complete in less than 2.5 h. At complete conversion of 2-methylglutaronitrile, the yields of 4-cyanopentanoic acid ammonium salt and 2-methylglutaric acid diammonium salt were 98.5% and 1.5% yields, respectively.

At the end of the reaction the product mixture was decanted from the catalyst beads, which were reused in an additional five consecutive batch reactions as described above. The rate of production of 4-cyanopentanoic acid in reaction six was 721 mM/h, and the reaction was complete in less than 2.5 h. At complete conversion of 2-methylglutaronitrile, the yields of 4-cyanopentanoic acid ammonium salt and 2-methylglutaric acid diammonium salt were 98.0% and 2.0% yields, respectively.

EXAMPLE 12

Total Turnover Number (TTN) for Immobilized *Acidovorax facilis* 72W Cell Nitrilase Into a 125 mL jacketed reaction vessel (temperature-controlled at 25° C.) was placed 16.5 g of immobilized *Acidovorax facilis* cell catalyst (prepared as described in Example 8). To the reaction vessel was added 72.1 mL of water and 11.4 mL (10.83 g, 1.0 M) of MGN, and the mixture stirred at 25° C. Samples (0.100 mL) were mixed with 0.400 mL of water, then 0.360 mL of a diluted sample was mixed with 0.040 mL of 0.75 M N-methylpropionamide in water and 0.020 mL of 6.0 N HCl. The resulting mixture was filtered (0.22 µm) and the filtrate analyzed by IPLC. After complete conversion of MGN, the product mixture and catalyst were decanted to a tared 250 mL beaker and the aqueous product mixture decanted from the catalyst. The remaining catalyst and product mixture heel was weighed and the weight recorded, then water was added to the catalyst to a final total weight (water and catalyst) of 88.6 g. The catalyst suspension was transferred back to the reaction vessel, 11.4 mL of MGN added, and the reaction repeated.

A total of sixty-seven consecutive batch reactions with catalyst recycle were run. There was no measurable loss of catalyst bead weight over the course of the sixty-seven recycle reactions, and 1001 g 4-CPA/g dcw *Acidovorax facilis* 72W cells were produced. The initial reaction rate was 142 mM 4-CPA/h, which corresponds to 237 IU of nitrilase activity, or 6.76 mg ($1.7 \times 10^{-7}$ mole) of 72W nitrilase. The amount of 4-CPA produced in 67 consecutive batch reactions was 6.6 moles, thus the total turnover number (TTN=moles product per moles enzyme) was $6.6/1.7 \times 10^{-7}$, or $3.9 \times 10^7$ TTN.

EXAMPLE 13

Expression of *Acidovorax facilis* 72W Nitrilase Coding Sequence in *Pichia pastoris*

A synthetic nitrilase gene (SEQ ID NO:16) (which encodes a protein sequence identical to that found in *Acidovorax facilis* 72W (SEQ ID NO:14)) was constructed using sixteen 90 bp oligomers (SEQ ID NOS:17–32) and the technique of PCR-mediated overlap extension. The synthetic gene optimizes the codon usage found in *Pichia pastoris*, which is considerably different from that found in the *A. facilis* 72W nitrilase gene sequence. After confirming by nucleotide sequencing, the synthetic nitrilase gene is subcloned into pGAPZA and into pPICZA (Invitrogen, San Diego, Calif.) at the EcoRI site. pGAPZA uses the constitutive *P. pastoris* GAP (glyceraldehyde-3-phosphate dehydrogenase) promoter to drive expression of foreign genes; pPICZA uses the methanol inducible *P. pastoris* AOXI (alcohol oxidase I) promoter to drive expression of foreign genes. Plasmids pGAP::nit and pAOX::nit are used to transform *P. pastoris* GS115 (Invitrogen) to zeocin resistance by spheroplast transformation essentially as described (Cregg et al., *Mol. Cell Biol.* (1985) 5:3376–3385). After appropriate growth and induction (only pAOX::nit requires induction), transformants producing nitrilase are identified by SDS-PAGE protein analysis of cells extracts prepared essentially as described (Sreekrishna et al., *Biochem* (1989) 28:4117–4125), and by enzyme activity assay as previously described (Examples 6 and 7).

EXAMPLE 14

Determination of *Acidovorax facilis* 72W Nitrilase as % of Total Soluble Protein A crude extract of *Acidovorax facilis* 72W was prepared by passage of a 25 wt % cell suspension through a french press as previously described (Example 1). Protein components in an aliquot of the soluble protein fraction of the crude extract were separated by gel electrophoresis (SDS-PAGE) performed under reducing conditions (5% β-mercaptoethanol) on a 10–15% SDS polyacrylamide gel. Following electrophoresis, the gel was treated for 15 min at 25° C. with a solution composed of 0.2% Coomassie Brilliant Blue dye, 30% methanol, and 10% acetic acid. Protein bands were visualized in the gel following de-staining with a solution composed of 30% methanol and 10% acetic acid. The protein bands in the gel were then integrated using an LKB Ultroscan XL Enhanced Laser Densitometer. The nitrilase band having a subunit MW of ca. 40 kd represented 3.4% of the total soluble protein detected on the gel.

EXAMPLE 15

Construction of SS1011 [MG1655(DE3):pnitex2] and its Nitrilase Activity

λDE3 prophage was site-specifically integrated into the chromosome of *E. coli* strain MG1655 (ATCC 47076) to yield strain MG1655(DE3). λDE3 lysogenization kit (Catalog No 69734-3, Novagen, Inc. Madison, Wis.) was used for this purpose according to manufacturer's instructions. MG1655(DE3) was transformed with plasmid pnitex2 described in Example 6 to yield SS1011. Strains SS1011 and SS1001 were grown in LB medium for 16–17 h. Whole cell nitrilase activity as shown in Table 5 was determined using a microliter plate-based spectrophometric assay performed at 35° C. that measures the hydrolysis of benzonitrile (9.5 mM, 0.1 M phosphate buffer, pH 7.0) to produce benzoic acid as indicated by the increase in absorption at 245 nm. The nitrilase activity units (IU) determined using this assay are typically 5–6 fold higher than those determined using the previously described methylglutaronitrile assay due to a combination of higher assay temperature (35° C. vs. 25° C.) and the relatively higher substrate specificity of the enzyme for benzonitrile.

TABLE 5

Nitrilase activity in *E. coli* transformants SS1001 and SS1011 determined by assay of hydrolysis of benzonitrile

| Transformant Catalyst | Nitrilase Activity (IU/g dry cell weight) |
|---|---|
| *E. coli* SS1011 (MG1655(DE3): pnitex2) | 3652 |
| *E. coli* SS1001 (BL21(DE3): pnitex2) | 4500 |
| *Acidovorax facilis* 72W (ATCC 55746) | 1491 |

---

What is claimed is:

1. An isolated nucleic acid fragment comprising a first nucleotide sequence encoding a polypeptide with nitrilase activity having at least 95% identity as compared to a polypeptide encoded by the sequence identified in SEQ ID NO:5, or a second nucleotide sequence comprising the complement of the first nucleotide sequence.

2. A chimeric gene comprising the isolated nucleic acid fragment of claim 1 operably linked to suitable regulatory sequences.

3. A plasmid pnitex2 contained in *E. coli* SS1001 having the designation ATCC PTA-1177.

4. An expression cassette comprising the chimeric gene of claim 2.

5. The expression cassette of claim 4 comprising plasmid pnitex2.

6. A transformed microorganism comprising the chimeric gene claim 2.

7. A transformed microorganism comprising the plasmid of claim 3.

8. A transformed microorganism comprising the expression cassette of claim 4.

9. The transformed microorganism of claim 8 wherein the expression cassette is chromosomally integrated.

10. The transformed microorganism of claim 9 further comprising suitable regulatory sequences.

11. The transformed microorganism of claim 10 wherein the suitable regulatory sequences comprise
   a) at least one promoter selected from the group consisting of the tryptophan operon promoter Ptrp of *E. coli*, a lactose operon promoter Plac of *E. coli*, a Ptac promoter of *E. coli*, a phage lambda right promoter PR, a phage lambda left promoter PL, a T7 promoter, a promoter of the AOX1 gene from *Pichia pastoris*, and a promoter of the GAP gene from *Pichia pastoris*, or is at least one strong promoter selected from the group consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*, and
   b) at least one ribosome binding site from a phage lambda CII gene or selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

12. The transformed microorganism of claim 11, wherein the host microorganism is selected from the group consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

13. A transformed microorganism *E. coli* SS1001 having the designation ATCC PTA-1177.

14. The transformed microorganism of claim 12, wherein the host microorganism is *E. coli* strains MG1655 (ATCC 47076), W3110 (ATCC 27325), MC4100 (ATCC 35695), or W1485 (ATCC 12435).

15. An isolated nucleic acid fragment encoding a polypeptide having the amino acid sequence of SEQ ID NO:5.

16. An isolated nucleic acid fragment comprising a first nucleotide sequence encoding a polypeptide with nitrilase activity having at least 95% identity as compared to a polypeptide encoded by the sequence identified in SEQ ID NO:5.

* * * * *